(12) United States Patent
Pfleger et al.

(10) Patent No.: US 8,379,918 B2
(45) Date of Patent: Feb. 19, 2013

(54) METHOD FOR PERCEPTION MEASUREMENT

(76) Inventors: Ernst Pfleger, Vienna (AT); Christoph Pfleger, Vienna (AT)

( * ) Notice: Subject to any disclaimer, the term of this patent is extended or adjusted under 35 U.S.C. 154(b) by 588 days.

(21) Appl. No.: 12/664,513

(22) PCT Filed: Jun. 12, 2008

(86) PCT No.: PCT/AT2008/000210
§ 371 (c)(1),
(2), (4) Date: Dec. 14, 2009

(87) PCT Pub. No.: WO2008/151346
PCT Pub. Date: Dec. 18, 2008

(65) Prior Publication Data
US 2010/0183205 A1   Jul. 22, 2010

(30) Foreign Application Priority Data
Jun. 12, 2007   (AT) .................................. A 911/2007

(51) Int. Cl.
*G06K 9/00*   (2006.01)
(52) U.S. Cl. .......................................... 382/103; 348/78
(58) Field of Classification Search .................. 382/103, 382/104, 107, 117; 348/78; 351/209, 210
See application file for complete search history.

(56) References Cited

U.S. PATENT DOCUMENTS

| | | | |
|---|---|---|---|
| 6,090,051 A | 7/2000 | Marshall | 600/558 |
| 6,120,461 A | 9/2000 | Smyth | 600/558 |
| 2005/0073136 A1 | 4/2005 | Larsson et al. | 280/735 |
| 2009/0086165 A1* | 4/2009 | Beymer | 351/210 |

FOREIGN PATENT DOCUMENTS

| | | |
|---|---|---|
| EP | 1 219 243 A1 | 7/2002 |
| EP | 1 300 108 A1 | 4/2003 |
| WO | WO03/024319 A2 | 3/2003 |
| WO | WO2006/024129 A1 | 3/2006 |
| WO | WO2006/108017 A2 | 10/2006 |

OTHER PUBLICATIONS

Krupinski et al.: Eye-movement study and human performance using telepathology virtual slides . . . , in: Human Pathology, vol. 37, 2006, pp. 1543-1556.
Sodhi et al.: On-Road Driver Eye Movement tracking usig Head-Mounted Devices, in: Proceedings ETRA 2002, Mar. 25-27, pp. 61-68.

* cited by examiner

*Primary Examiner* — Andrew W Johns
(74) *Attorney, Agent, or Firm* — Henry M Feiereisen LLC

(57) ABSTRACT

In a procedure for measuring perception, first visual coordinates of a first point of vision assigned to a first visual field are processed, and second visual coordinates of a second point of vision assigned to a second visual field image, are processed. For determining the visual attention to certain areas of the surroundings, the second visual coordinates are examined together with the first visual coordinates in a comparison device to check whether they fulfill a fixation criterion. If the first and second points of vision fulfill the fixation criterion, they are assigned to a first fixation associated with ordered perception. Otherwise, they are assigned to a first saccade associated with aleatoric perception.

33 Claims, 24 Drawing Sheets

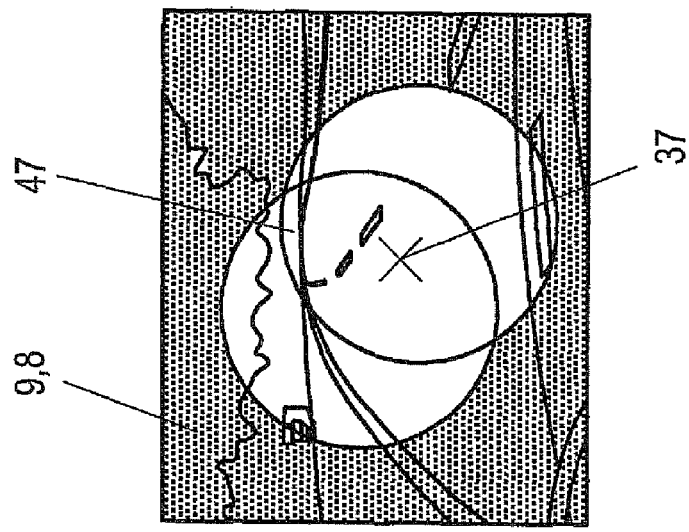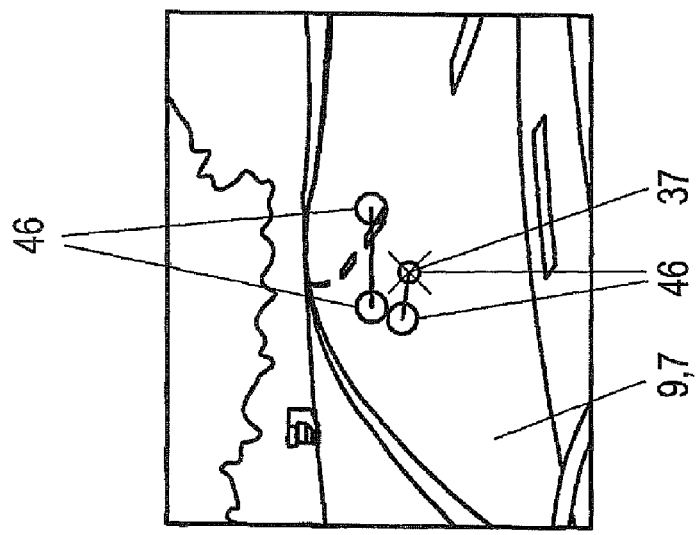

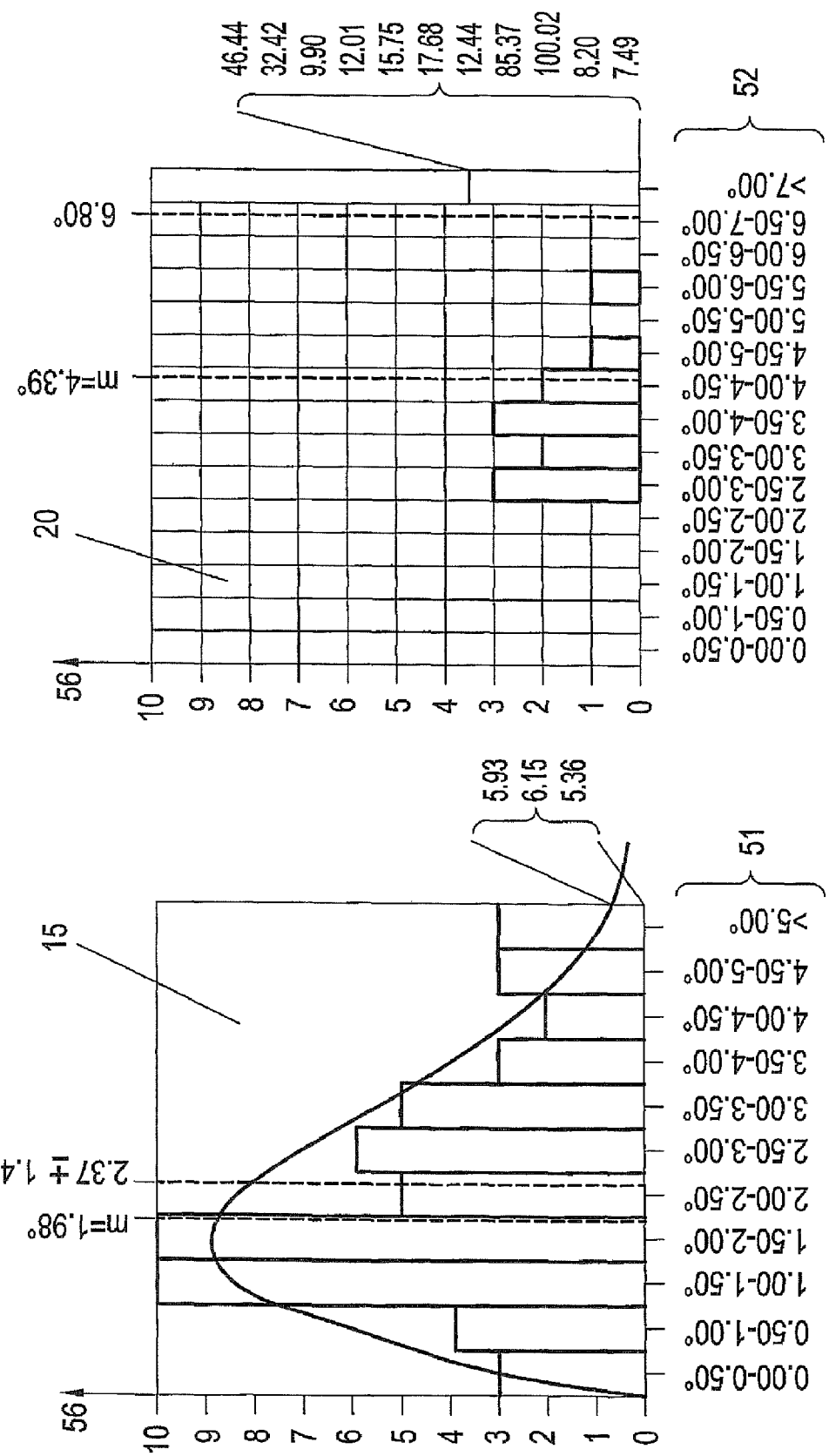

METHOD FOR PERCEPTION MEASUREMENT

CROSS-REFERENCES TO RELATED APPLICATIONS

This application is the U.S. National Stage of International Application No. PCT/AT2008/000210, filed Jun. 12, 2008, which designated the United States and has been published as International Publication No. WO 2008/151346 and which claims the priority of Austrian Patent Application, Serial No. A 911/2007, filed Jun. 12, 2007, pursuant to 35 U.S.C. 119 (a)-(d).

BACKGROUND OF THE INVENTION

The invention relates to a method for perception measurement, in particular for measuring the visual attention of an individual.

An eye tracking system can be used to determine the area or location on the visual field on which the individual's point of vision lies. This type of eye tracking system determines visual coordinates, in other words coordinates within the visual field of the individual, on which the individual's point of vision is focussed. An extremely exceptional and precise procedure to determine these visual coordinates is identified from EP 1 300 018 B1.

The purpose of the invention is therefore a method for perception measurement, in particular for measuring the visual attention of an individual of the type described in the introduction, wherein the visual attention for certain areas can be measured as accurately as possible.

SUMMARY OF THE INVENTION

In accordance with the invention, this is achieved by a method for measuring visual perception, having the steps of processing at least first visual coordinates of a first point of vision assigned to a first field-of-view image and determined, for example by using an eye tracking system, processing at least second visual coordinates of a second point of vision assigned to a second field-of-view image, with the second field-of-view image being recorded after the first field-of-view image, examining the second visual coordinates of the second point of vision together with the first visual coordinates of the first point of vision in a comparison device and checking whether they fulfill at least one predetermined first fixation criterion, assigning the first and second points of vision, provided they fulfill the at least one first fixation criterion, to a first fixation assigned to an ordered perception, and marking the first and second points of vision as such, and assigning the first and second points of vision, if they do not fulfill the at least one first fixation criterion, to a first saccade, to be assigned to aleatoric perception, and marking the first and second points of vision as such.

The perception of the test subjects or their attention on certain surrounding areas can therefore be measured on a scientific basis. By using predefined surroundings, it is possible to determine exactly the areas which are perceived reliably and consciously by the test subjects and the areas that are given a subordinate and secondary glance. This enables the quality of surroundings, such as a workplace, to be assessed and measured, particularly in safety-related or hazardous areas, for example a road, particularly on bends, construction sites and/or thoroughfares, a user screen interface, switchboards, a machine control panel, the cockpit design of motor vehicles and aircraft, and/or an advertising medium such as an image or text display or television commercials. As a result, areas in the surroundings and the environment, which endanger life and limb, are assessed and measured on the basis of their degree of perceptibility, and reshaped in order to improve the recording of important information. The run of a road can be optimised during planning with regards to lowering the risk of accidents, important traffic signs, such as stop signs, can be positioned at specific locations where road users demonstrate a high degree of perception based on scientific research. Work surroundings can be specifically designed so that important and safety-related control elements, notices and operating elements encourage ordered perception by the user; advertising can be adjusted to the ordered perception of the observer.

The subclaims, which form part of the description along with Claim 1, concern additional beneficial embodiments of the invention.

BRIEF DESCRIPTION OF THE DRAWING

The invention is described in greater detail with reference to the enclosed drawings, which only present the preferred embodiments by way of example. This shows:

FIG. 9 a first preferred output of a visual field video with a first and a second circuit;

FIG. 10 a second preferred output of a visual field video with a third circuit;

FIG. 11 a third preferred output of a visual field video with a fourth circuit;

FIG. 13 a first preferred output of the frequency of the fixations determined depending on the angle of fixation;

FIG. 14 a first preferred output of the frequency of the saccades determined depending on the angle of saccade;

DETAILED DESCRIPTION OF PREFERRED EMBODIMENTS

Figure 1:
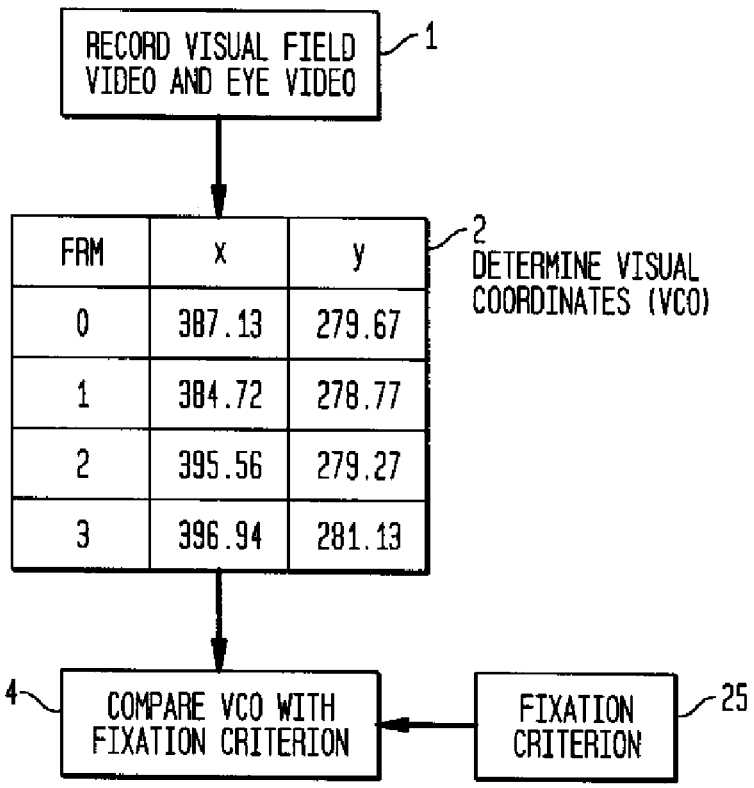
FIG. 1 a block diagram of the first embodiment of the invention.

FIGS. 1, 3, 4 and 5 each show block diagrams of preferred embodiments of a method for perception measurement, in particular for measuring the visual attention of an individual, wherein at least first visual coordinates of a first point of vision (37), associated to a first image of a visual field, and at least second visual coordinates of a second point of vision (38), associated to a second image of a visual field, are processed, first and second visual coordinates being detected essentially by an eye tracking system. The invention is characterised in that the second image of a visual field is recorded after the first image of a visual field and that the second visual coordinates of the second point of vision (38) are analysed with the first visual coordinates of the first point of vision (37) in a comparative device for meeting at least one first predetermined fixation criterion (25). When the first fixation criterion (25) is fulfilled, the first and second points of vision (37, 38) are allocated to a first fixation (48) that can be associated to ordered perception, and when the first fixation criterion (25) is not fulfilled, the first and second points of vision (37, 38) are marked and allocated to a first saccade associated with aleatoric perception.

The perception of the test subjects or their attention on certain surrounding areas can therefore be measured on a scientific basis. By using predefined surroundings, it is possible to determine the areas which are perceived reliably and consciously by the test subjects and the areas that are given a subordinate and secondary glance. This enables the quality of surroundings, such as a workplace, to be assessed and measured, particularly in safety-related or hazardous areas, for example a road, particularly on bends, construction sites and/or thoroughfares, a user screen interface, switchboards, a machine control panel, the cockpit design of motor vehicles and aircraft, and/or an advertising medium such as an image or text display or television commercials. As a result, areas in the surroundings and the environment, which endanger life and limb, are assessed and measured on the basis of their degree of perceptibility, and reshaped in order to improve the recording of important information. The run of a road can be optimised during planning with regards to lowering the risk of accidents, important traffic signs, such as stop signs, can be positioned at specific locations where road users demonstrate a high degree of perception based on scientific research. Work surroundings can be specifically designed so that important and safety-related control elements, notices and operating elements encourage ordered perception by the user; advertising can be adjusted to the ordered perception of the observer.

The concepts chosen in the current embodiment with regards to the first, second, third, etc. visual coordinates, points of vision, fixations, saccades, circuits, angle of fixation and/or saccade and so on are in no way preferred so as to restrict the method sequence to just two of the indicated features or to understand a single method sequence, but instead as a description of the individual sequence of a predetermined and often repeatable method.

Figure 22:
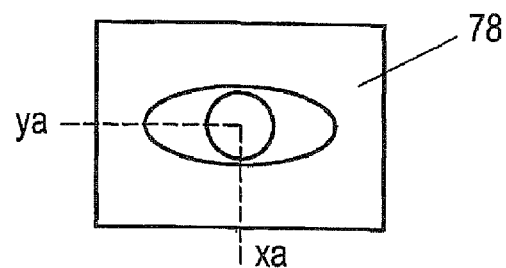
FIG. 22 a schematic representation of the eye diagram.
Figure 23:
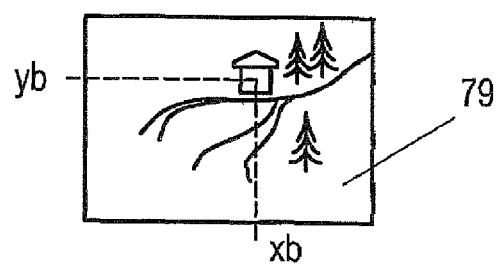
FIG. 23 a schematic representation of a visual field diagram.

The method according to the invention processes data, which is recorded using a so-called eye tracking system. Such an eye tracking system is represented schematically in FIG. 21. A highly exceptional eye tracking system is described in EP 1 300 108 A1. Such an eye tracking system, which is described briefly below, works according to a method for recording, evaluating and analysing glance sequences of a test subject using an eye tracking system, wherein the visual field of the test subject is recorded using a first camera (76) rigidly connected to the head (80) of the test subject so that it faces forward and is recorded in a visual field video, the movement of the pupils of the test subject is recorded with a second camera (77), which is also rigidly connected to the head (80) of the test subject, and is recorded in an eye video, and the eye video and the visual field video (9) are recorded on a video system and time-synchronised, wherein for each individual image of the eye video, therefore for each eye image (78) the pupil coordinates xa,ya are determined, the correlation function K between pupil coordinates xa,ya on the eye video and coordinates xb,yb of the corresponding point of vision B, i.e. the point the test subject fixes on, on which the visual field image (79) of the visual field video (9) is determined, and after determining the correlation function K for each individual image from the pupil coordinates xa,ya on the eye video, the coordinates xb,yb of the corresponding point of vision B on the visual field video are extrapolated, wherein to determine the pupil coordinates xa,ya for each individual image of the eye video with a visual detection programme, the contrasts of the pupils to the surroundings are automatically recorded, all points of the individual image, which are darker than a predefined degree of darkness, are identified, these points record and limit an area of darkness corresponding to the pupil and the focus of the area of darkness, which corresponds to the middle of the pupil with the pupil coordinates xa,ya, is determined. If preferred it can be defined that a predetermined number of points on the edge of the pupil are selected, which can be easily and reliably identified due to their contrast with the surroundings, and that these points are accepted as part of an ellipsis, wherein the focus or centre of an ellipsis is calculated around the circumference of which the predetermined number of points lie. This achieves a particularly high level of accuracy, which is far beyond the state of the art of known eye tracking systems. Consequently errors, which can be caused by reflections on the eye, have no influence on the measured result. FIG. 22 shows a schematic example for an eye image (78) of an eye video with the pupil coordinates xa,ya. FIG. 23 shows a schematic example for a visual field image (79) with the coordinates xb,yb of the first point of vision (37). The purpose of the eye tracking system is to represent with the greatest possible accuracy the point on which the visual field of an individual fixes, i.e. the exact point to which the test subject's interest or attention is drawn.

The visual field is recorded by a first forward-facing camera (76) rigidly connected to the head (80) of the test subject. The movement of the pupils of the test subject is recorded by a second camera (77), which is also rigidly connected to the head (80). Rigidly connected in this context means that both cameras (76, 77) are attached to the head (80) of the test subject in such a way that they move with the test subject and follow all of the movements made by the test subject without restricting the freedom of movement of the subject's head and eyes in any way. By evaluating these two recordings it is possible to ascertain with considerable accuracy the point on which the test subject is fixed. Statements can also be made regarding visual attention, visual connections and visual absences.

Such eye tracking systems are preferred for use in the safety sector, particularly in the area of accident research, as well as in the area of advertising, sport or other human physiological tests.

Overall, research into eye glance behaviour represents a significant building block in the research of physiological causes of accidents. For example, comprehensive visual tests can ascertain new findings to explain and reconstruct accidents in terms of human performance limits.

As a result, particularly hazardous points in road traffic can be investigated with the eye tracking system. A test subject fitted with such an eye tracking system travels through the hazardous point and eye glance behaviour is recorded. The sum of the glances analysed is referred to below as a glance sequence. By analysing eye glance behaviour it is possible to ascertain which signposts or traffic signs are ignored because of their unfavourable positioning or where at a junction there are points that are particularly ignored. In the area of occupational safety, e.g. on construction sites, tests can determine which hazards are perceived late by the test subject and which safety precautions would be required. A further important area of application for eye tracking systems is the analysis of advertisements or television commercials. In this area it is also possible to determine with considerably accuracy which messages, text, logos, etc. are perceived by the test subject, for how long and in what order.

Figure 21:
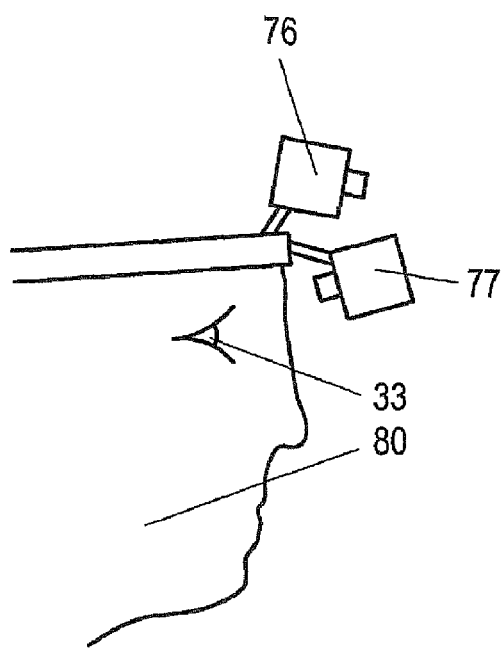
FIG. 21 a schematic representation of the part of an eye tracking system connected to the head of a test subject.

FIG. 21 shows part of an eye tracking system for the performance of a preferred method for determining the point of vision or visual coordinates (VCO). The visual field of the test subject is recorded by a first forward-facing camera (76) rigidly connected to the head (80) of the test subject. This first camera (76) therefore gives an approximate image of the test subject's line of vision, which is defined purely by the position of the head (80). The first camera (76) can be a CCD colour camera, for example, which records the majority of the test subject's visual field.

If preferred the first camera (76) and/or the second camera (77) can also be controlled using software and thus be adapted to the external conditions of use. This ensures that by directly recording the pupils there is no distortion in the pupil image and through the direct proximity to the eye (33) a large image is generated and the set-up can be kept smaller overall. Current methods represent a considerable source of inaccuracy due to their size and generally poor assignment of the pupil point. This results not only in difficulties in the weight of the eye tracking system, but also general restrictions on the eye glance behaviour of the test subject, which are avoided by the method in the present invention. As a result, the eye tracking system in the present invention can also be used by test subjects with different clothing and protective measures, such as a helmet, without restriction. It is therefore possible to use different lightweight cameras (76, 77) with different lenses depending on the test requirements.

The preferably high-quality cameras, which are used in the preferred system, are preferably fitted with a control unit that allows automatic white balancing, colour balancing and exposure. These values are preferably adjustable by hand. This control unit allows the image quality to be optimally adapted to the test conditions. This ensure a very high image quality for further analysis. There is also an option to zoom in on the image section digitally. Other setting options generally only have a limited influence on the generated image.

The movement of the pupils of the test subject is recorded by a second camera (77), which is also rigidly connected to the head (80) and which is directed at one of the two eyes (33) of the test person. The second camera (77) can, for example, be a B&W CCD camera and can record the eye movements of the right eye. The pupil position by the second camera (77) is recorded directly by the eye tracking systems show in the figures, wherein the second camera (77) is pointed directly at the eye (33) of the test person. The pupil position can also be recorded via optical refraction systems such as mirrors or glass fibre cables, wherein the image of the eye (33) is refracted to the second camera (77).

Both cameras (76, 77) are attached, for example, to a helmet or a pair of glasses or a similar support that is easy to put on and remove, which is rigidly connected with the head (80) of the test person. As explained above, rigidly connected means that the support and both cameras (76, 77) follow all of the movements of the head (80), wherein the freedom of movement of the head (80) and the eyes (33) is not restricted in any way. Attaching the camera (76, 77) to a pair of glasses as an easy support to put on and remove with direct recording on a mobile recording device allows a particularly high level of mobility of the test subject and allows a much higher range of testing than with standard systems.

Naturally it is also possible to fit several second cameras (77), for example, to record both pupils of the test subject. Several first cameras (76) can also be fitted to record the full visual field of the test subject, if the focal distance of an individual first camera (76) is not sufficient for this. This allows individual image sequences to be recorded and, as described below, to be evaluated and analysed. The term glance sequence refers here to the sum of the recorded and analysed glances.

Using both cameras (76, 77) provides two video signals that are referred to in the following as eye video and visual field video and represented schematically in FIGS. 22 and 23, which are recorded on a video system. The term video system covers all set-ups that are suitable for recording film data. Analogue film materials such as video tapes or digital storage media such as DVDs or similar can also be used. The storage of individual images in the memory of a computer is considered recording within the meaning of this invention. Different analogue or digital film formats can be used such as DV, AVI or MPEG2. When using CCD cameras, all image information is preferably recorded on a digital video system, for example on two mini DV recorders.

In the preferred embodiment, the cameras 76, 77) and the video system are a hard-wired connection or via a radio link. This enables the wireless transmission of the video signals to the video system. Consequently, this does not restrict the test subject's movement when walking, cycling or working, e.g. on scaffolding or construction sites.

It is important that both video signals are synchronised, i.e. so that the corresponding individual image of the visual field video (9) can be found and vice versa for each individual image of the eye video. Synchronisation can be carried out with a periodic signal generator and time code. The recording method is preferably synchronised with a tone pulse, which is recorded on the respective audio tracks. This method enables other external devices, such as UDS data recorders, GPS systems, etc. to be synchronised in order to synchronise other technical and medical variables such as the current geographical position or also heart or pulse frequency, skin resistance, breathing frequency, etc. of the test subject directly with the eye glance behaviour. Synchronisation is important for the subsequent processing or evaluation of both video signals according to the invention.

The preferred method determines the precise coordinates (xa,ya) of the pupil centre point in the eye video using an image detection programme. This determines the pupil coordinates (xa,ya) for each individual image of the eye video. The pupil coordinates (xa,ya) in an individual image of the eye video are sketched in FIG. 22. The pupil coordinates (xa,ya) are preferably determined automatically with an image detection programme. It records the contrasts of the pupils with the surroundings for each individual image of the eye video and searches for all of the points of the individual image, which are darker than a predetermined degree of darkness. With these points it is possible to record and delimit a dark area and ultimately determine the focus of this dark area automatically. As the dark area corresponds to the pupils of the test subject, the focus of the dark area represents the centre of the pupils. The image detection system preferably offers setting options for the corresponding contrasts and the degree of darkness so that a particularly high degree of accuracy can be achieved for all individual images. As already mentioned above, it can be defined that a predetermined number of points on the edge of the pupil are selected, which can be easily and reliably identified due to their contrast with the surroundings, and that these points are accepted as part of an ellipsis, wherein the focus or centre of an ellipsis is calculated around the circumference of which the predetermined number of points lie. The best contrast in the form of a grayscale depth can thus be guaranteed for each individual image under different exposure conditions, which improves the reliability of the pupil coordinates (xa,ya). The grayscale depth is any value, which lies in digital format between 1 and 256, for example, and the percentage share of black and white defined at an image point. The highest possible value corresponds to a completely black point, the lowest value to a completely white point. As the pupils probably never reach the full black value during the recording, a value must be defined that corresponds to the real existing pupil grey, at least for this image. The threshold demarcates all image points that are lighter than the defined grayscale value, all darker areas are included in the focus determination. Three parameters allow the threshold definition to be optimised. As the exposure conditions often change considerably during the tests conducted within a sequence, this threshold definition is preferably also possible individually for each image. All settings can be stored in a file according to the high requirements for each image of the sequence. The method according to the invention allows a particularly high level of accuracy when assigning the pupil coordinates (xa,ya) to the visual field. The respective degree of accuracy can be visualised.

To achieve a particularly high degree of accuracy for the calculated pupil coordinates and thus to achieve a particularly accurate determination of the visual attention, a preferred embodiment of the invention provides for a correction of visual defects, particularly lens rectification, perspective correction, image field correction and/or correction of the so-called aberrations, such as spherical aberration, chromatic aberration, dispersion, asymmetry errors (coma), astigmatism of uneven groups (astigmatism), curvature of image field, domed picture, optical distortion, and/or monochromatic imaging errors.

In addition, an infrared filter can be placed in front of the camera to improve the accuracy of the localisation of the pupil centre. This improves the contrasts in the eye video. The IR filter has two advantages: Firstly, the eye (33) is illuminated with infrared LEDs (IR LED), which guarantee good contrasts for the eye camera and for further processing, even in absolute darkness. The filter allows the light emitted by the LED on to the camera chip, but all other spectral ranges of light are attenuated according to the filter transmission curve. Secondly, the reflections on the pupils caused by sunlight, which have an extremely negative impact on focussing, primarily exist in the blue spectral range. Here again the filter reduces the reflections on the pupils, which are caused by sunlight.

In a further advantageous embodiment of the preferred method, an additional manual inspection is carried out following the automatic determination of the pupil coordinates (xa,ya). If automatic recognition fails (for example sudden light reflexes on the eye surface, etc.), a processor can manually change the image processing parameters. It is also possible to directly correct the pupil coordinates (xa,ya).

The pupil coordinates (xa, ya) for each individual image of the eye video are obtained, for example, in the form of a Cartesian pair of values. Naturally, other co-ordinate systems such as polar coordinates and so on can also be used. As both cameras (76, 77) are rigidly connected with the head (80) of the test subject, a specific position of the pupil or pupil centre in the eye video always corresponds to an accurately defined point of vision B in the visual field video (9). The eye video and visual field video (9) can therefore be used to calculate the point on which the test subject is fixed. When assigning pupil coordinates (xa,ya) to coordinates (xb,yb) of the corresponding point of vision B, i.e. of the point on which the test subject fixes, the visual field video must be used to determine the correction function K initially between then two pairs of coordinates (xa,ya) and (xb,yb). The correlation between pupil coordinates (xa,ya) and point of vision B on the visual field video is carried out using a test series (calibration). In this case the test subject fixes the row according to specific predefined pass points P. The correlation function K between pupil coordinates (xa,ya) and coordinates (xb,yb) in the visual field video is created on the basis of the data measured here.

In the preferred method, the correlation function K between pupil coordinates (xa,ya) on the eye video and the coordinates (xb,yb) of the corresponding point of vision B on the visual field video 9 is determined automatically. One or more sample glance sequences of the test subject are first taken at one or more specific predefined pass points P. A sample glance sequence is a glance sequence that is taken purely for calibration purposes and during which the test subject looks at predefined pass points P. For example, a specific pass point P can be marked on a wall. In order to achieve the best possible contrast, a black mark on an otherwise white surface can be chosen as pass point P. Pass point P is normally a cross or a light point or similar. The test subject is instructed to fix on this pass point P, wherein the visual field and the eye of the test subject are recorded by both cameras (76, 77). This allows several pass points P to be defined.

As the point of vision B on the recorded visual field video of the sample glance sequence is determined by the known pass point P, the correlation function K between the pupil coordinates (xa,ya) on the eye video and the coordinates (xb,yb) of the corresponding point of vision B can be determined on the visual field video. This is achieved by determining the pupil coordinates (xa,ya) in the eye video according to the method described above for each individual image in the eye video. The coordinates (xb,yb) of the pass point P in the corresponding individual image are also determined on the visual field video. This is preferably carried out using an image detection method and/or a pattern detection method, which determines coordinates (xb,yb) of the pass point P, which can be uniquely identified by its contrast on the visual field video. However, it is also possible to determine the coordinates (xb,yb) of the pass point P in the visual field video for each individual image by hand, for example by clicking the mouse. This enables the sample glance sequence to be evaluated even if the surrounding conditions are poor, wherein automatic determination of the coordinates (xb,yb) of pass point P is not possible, for example due to an irregular background.

As a result, the pupil coordinates (xa,ya) in the individual image of the eye video can be assigned the coordinates (xb, yb) of the pass point P in the corresponding individual image of the visual field video. The corresponding coordinates in the eye and visual field videos are determined and stored for each individual image of the sample glance sequence. All of the data records obtained are used to correlate by quadratic regression the pupil coordinates (xa,ya) on the eye video and the coordinates (xb,yb) of the corresponding point of vision B on the visual field video, wherein other methods such as linear regression or stochastic models can be used for the correlation. This gives you a correlation function K: (xa,ya)→(xb, yb), which uniquely assigns a specific set of pupil coordinates (xa,ya) on the eye video to the corresponding coordinates (xb,yb) of point of vision B in the visual field video.

For the best possible accuracy of the correlation function K, at least 25 different positions of the pass point P should be used. Above 100 different pass point positions, the accuracy achieved hardly increases and consequently it is not logical to increase the number of pass point positions above this. Therefore between 25 and 100 pass point positions should preferably be used. The determined correlation function K can be used to generate all further video sequences of the same test series, i.e. wherein there are no changes concerning the camera positions on the head of the test subject. Through the digital correlation of both pairs of coordinates, it is possible to determine non-linear correlations.

After calibrating the eye tracking system, it is possible to determine and analyse individual glance sequences. Once the correlation function K has been determined, the pupil coordinates (xa,ya) on the eye video for each individual image are used to extrapolate the coordinates (xb,yb) of the corresponding point of vision B of the visual field video.

By combining the eye video and the visual field video (9) in a results video, technical software can position the calculated point of vision B as centre points of attention on the visual field video (9). By determining the coordinates (xb,yb) of the point of vision B according to the invention, it is possible to depict the centre point of attention with great accuracy. The point of vision B can be recorded accurately on the visual field video (9). The point of vision B is preferably indicated on the visual field video (9) by a clearly visible mark such as a cross.

By using a method according to the invention it is possible to determine which areas in the surroundings of a test subject is given their visual attention, which areas in the surroundings are actually perceived by the test subject, and which areas the test subject glances at or scans, but so briefly or so far away that there is no ordered perception by the test subject. Consequently, because the test subject has glanced at an area he or she will not have registered any of the contents of this area. Areas in which ordered perception takes place are referred to below by the term fixation. Areas in which eye movement occurs and in which no ordered perception takes place are referred to below by the term saccade.

Figure 2:
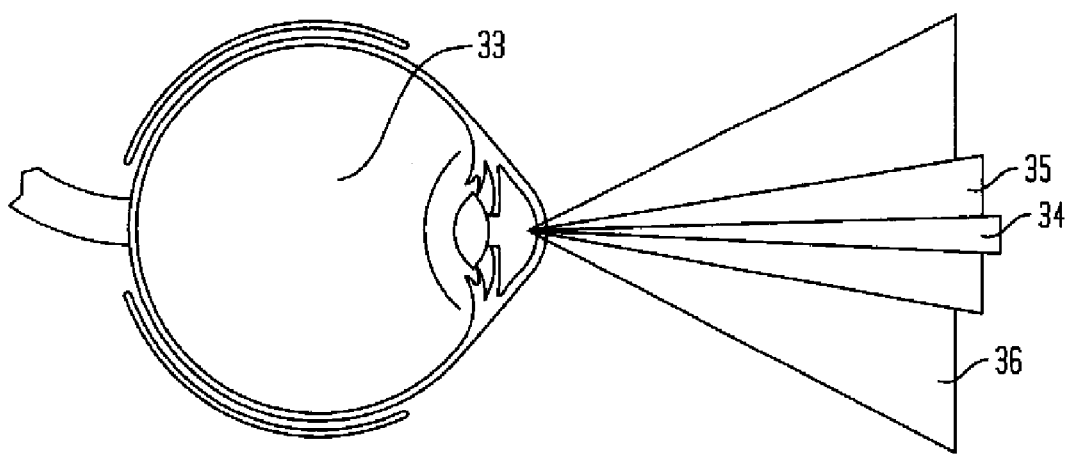
FIG. 2 a human eye in cross-section.

FIG. 2 shows a cross-section of a human eye (33), wherein areas of different acuteness of vision are identified. The most important area here is the so-called foveal area (34), which merely consists of a closely adjoining central optical axis, and in which the highest acuteness of vision is possible, and therefore also combines the ordered perception of visual stimulation. Standard definitions for the foveal area (34) used currently assume an initial viewing angle (41) of approximately 1° around the optical axis. As explained elsewhere in this document, the first viewing angle (41) of the foveal area (34) depends considerably on the focus and the surroundings. The foveal area (34) is surrounded by the so-called parafoveal area (35) in which the subject can still perceive coarse patterns. The so-called peripheral area (36) surrounding this parafoveal area (35) is only sensitive to movement. The eye cannot perceive a pattern or an object in this peripheral area (36).

In the method according to the invention, directly following points of vision (37, 38) are at least tested and compared in a comparison device in relation to compliance with at least the first fixation criterion (25). The comparison device can be any suitable device. Preference is given to devices that include electronic logic modules or so-called logic gates, which allow a comparison of input data based on Boolean algorithms. Particular preference is given to devices that use this type of electronic logic modules in integrated form, particularly in the form of processors, microprocessors and/or programmable logic controllers. Particular preference is given to comparison devices that are implemented in a computer.

The comparison device processes so-called visual coordinates, which can be abbreviated in the following as VCO, and which can be determined based on a correlation function described above between a visual field image (79) and an eye image (78), wherein other methods or procedures can be used to determine these VCO. FIG. 1 with the reference sign 2 gives a list of possible VCO for individual visual field images, where Frm is an abbreviation for frame, as Cartesian coordinates.

Figure 6:
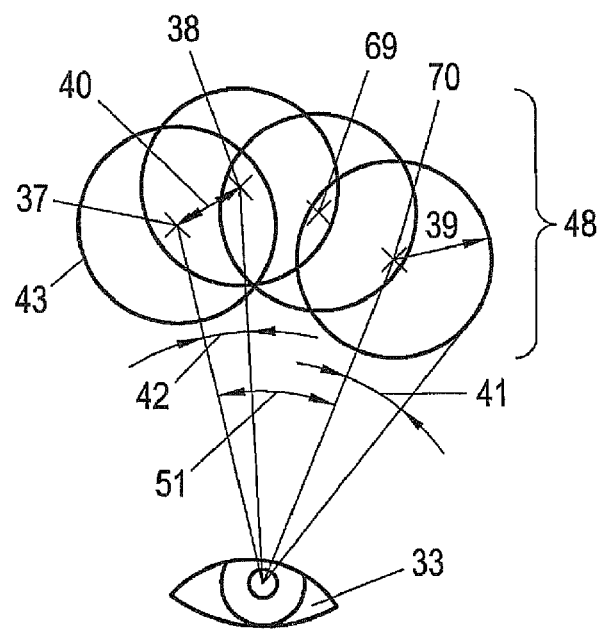
FIG. 6 a schematic representation of eye glance behaviour for fixation.

The first fixation criterion (25) can be any type of criterion, which allows a differentiation between fixations and saccades. The preferred embodiment of the method according to the invention provides that the first fixation criterion (25) is a predefinable first distance (39) around the first point of vision (37), that the first relative distance (40) between the first point of vision (37) and the second point of vision (38) is determined, and that if the first relative distance (40) is less than the first distance (39), the first and second points of vision (37, 38) are assigned to the first fixation (48), therefore as long as a second point of vision (38) following a first point of vision (37) remains within the foveal area (34) of the first point of vision (37) and thus within the area of ordered perception of the first point of vision (37), ordered perception is not interrupted and thus continues to fulfil the first fixation criterion (25). This is therefore a first fixation (48). A particularly preferred embodiment of the method according to the invention provides that the first distance (39) is a first viewing angle (41), which preferably describes an area (34) assigned to foveal vision, in particular a radius between 0.5° and 1.5°, preferably approximately 1°, and that the distance between the first point of vision (37) and the second point of vision (38) is a first relative angle (42). Based on the visual coordinates determined using an eye tracking system, it is possible to determine saccades and fixations (48, 49) simply and accurately. FIG. 6 shows a first fixation (48), for example, which is formed from a sequence of four points of vision (37, 38, 69, 70). FIG. 6 also shows the first distance (39), the first viewing angle (41), the first relative distance (40) and the first relative angle (42). Around each of the four points of vision (37, 38, 69, 70) is a first circle (43) with the radius of the first distance (39), wherein it is clearly shown that the following point of vision (38, 69, 70) lies within the first circle (43) with radius first distance (39) of the preceding point of vision (37, 38, 69), and thus the preferred first fixation criteria (25) is met. In order to adapt to objects that are perceived differently or to different people and/or conditions, a further updated version of the invention provides that the first fixation criterion (25), particularly the first distance (39) and/or the first viewing angle (41), can be predefined.

Figure 7:
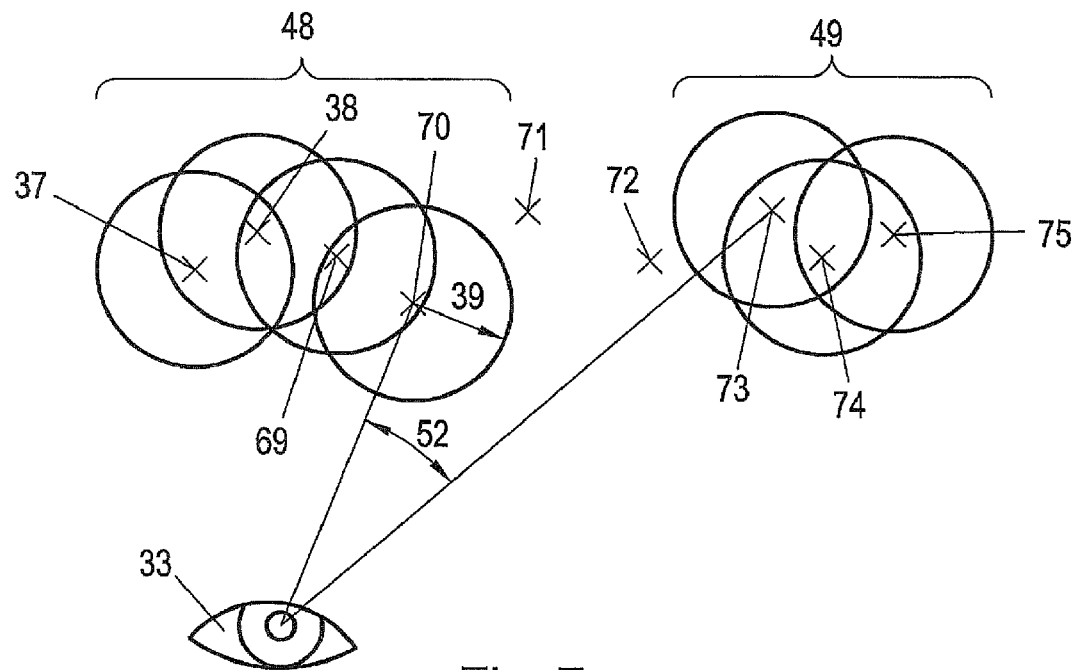
FIG. 7 a schematic representation of eye glance behaviour with a sequence for initial fixation, a saccade and a second fixation.

FIG. 7 shows a viewing sequence in which not all points of vision (37, 38, 69, 70, 71, 72, 73, 74, 75) satisfy the first fixation criterion (25). The first four points of vision (37, 38, 69, 70) satisfy the fixation criterion (25) and together form the first fixation (48), wherein the following three points of vision (71, 72, 73) do not satisfy the first fixation criterion (25). Only the fourth point of vision (74) following the first fixation (28) satisfies the first fixation criterion (25) compared to the third point of vision (73) following the first fixation (48). The third point of vision (73) following the first fixation (48) is therefore the first point of vision (73) of the second fixation (49), which is formed from a total of three points of vision (73, 74, 75). FIGS. 6 and 7 show illustrative examples, although fixations (48, 49) can occur in natural surroundings with a variety of individual points of vision. The area between the last point of vision (70) of the first fixation (48) and the first point of vision (73) of the second fixation (49) forms a saccade, therefore an area without perception. The angle between the last point of vision (70) of the first fixation (48) and the first point of vision (73) of the second fixation (49) is referred to as the first saccade angle (52).

FIG. 1 shows a block diagram for a method according to the invention, wherein in the first step (1) a visual field video (9) and an eye video are recorded using an eye tracking system. In a second step (2) the VCO are determined from the visual field video and the eye video, which are compared in a further step (4) in the comparison device with the defined, saved, importable or predefinable first fixation criterion (25). The points of vision (37, 38) assigned to a saccade or a fixation (48, 49) can now be output for further evaluation, processing or representation. In particular, it can be provided that the first and the second point of vision (37, 38) can be output and marked as the first fixation (48) or the first saccade.

In the comparison device, two at least directly subsequent visual field images or assigned VCO are compared. By preference it must be provided that the second visual field image has been recorded after a predefinable first period of time, in particular between 0.005 s and 0.1 s, preferably between 0.02 s and 0.04 s, following the first visual field image. Based on the movement resolution of the human eye (33) in the foveal area (34), which is only approximately 25 Hz, it is preferred that the time between two directly following visual field images is approximately 0.04 s. Depending on the required resolution, further visual field images can be recorded and the time between two directly following visual field images can be reduced, wherein a higher movement resolution is achieved, and/or a predefinable number of visual field images can be skipped, or a lower time resolution can be used for recording, wherein the movement resolution falls, along with the expenditure. By comparing the directly following visual field images, it is possible to achieve a high movement resolution as well as a low system complexity, as image selection systems and internal buffers can be avoided.

Figure 3:
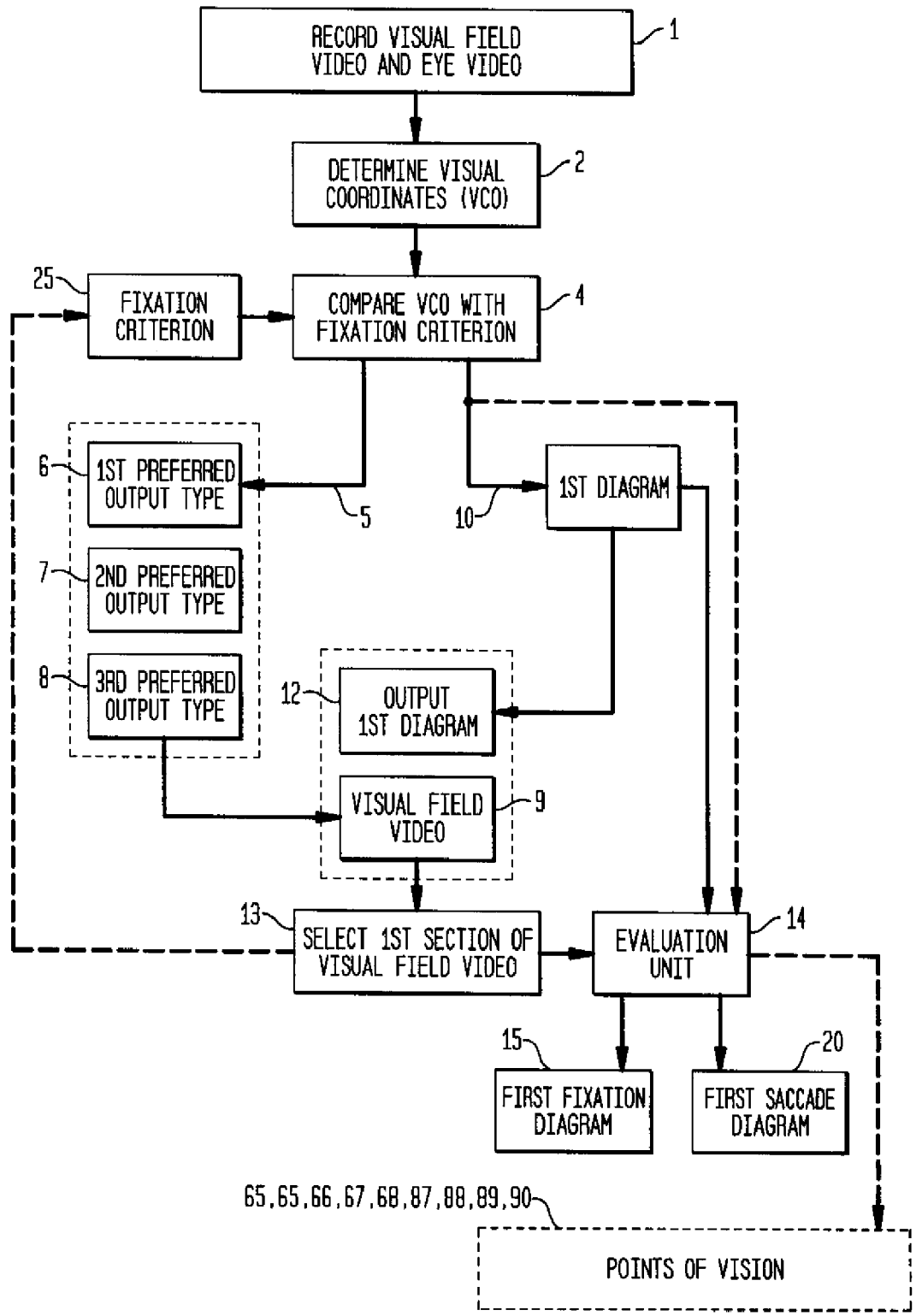
FIG. 3 a block diagram of a second embodiment of the invention.

FIG. 3 shows a block diagram of a highly preferred embodiment of the method according to the invention, wherein the method steps according to the method described above under FIG. 1 provide for subsequent processing of the calculated data, therefore whether or not a point of vision (37, 38) is assigned to a fixation (48, 49) or a saccade. It is provided that the first relative distance (40) is output together with the points of vision (37, 38) labelled as the first fixation (48) and the first saccade respectively. The data is prepared for the first output (10) in a first diagram (11) and/or for second output (5) on a visual field video (9), whereby it is preferred that a visual field video (9) recorded by the eye tracking system to determine the visual coordinates of points of vision (37, 38) is output and that at least the points of vision (37, 38) for the first fixation (48) or the first saccade are depicted in the visual field video (9), wherein it is possible to evaluate the visual perception quickly and simply.

Figure 12:
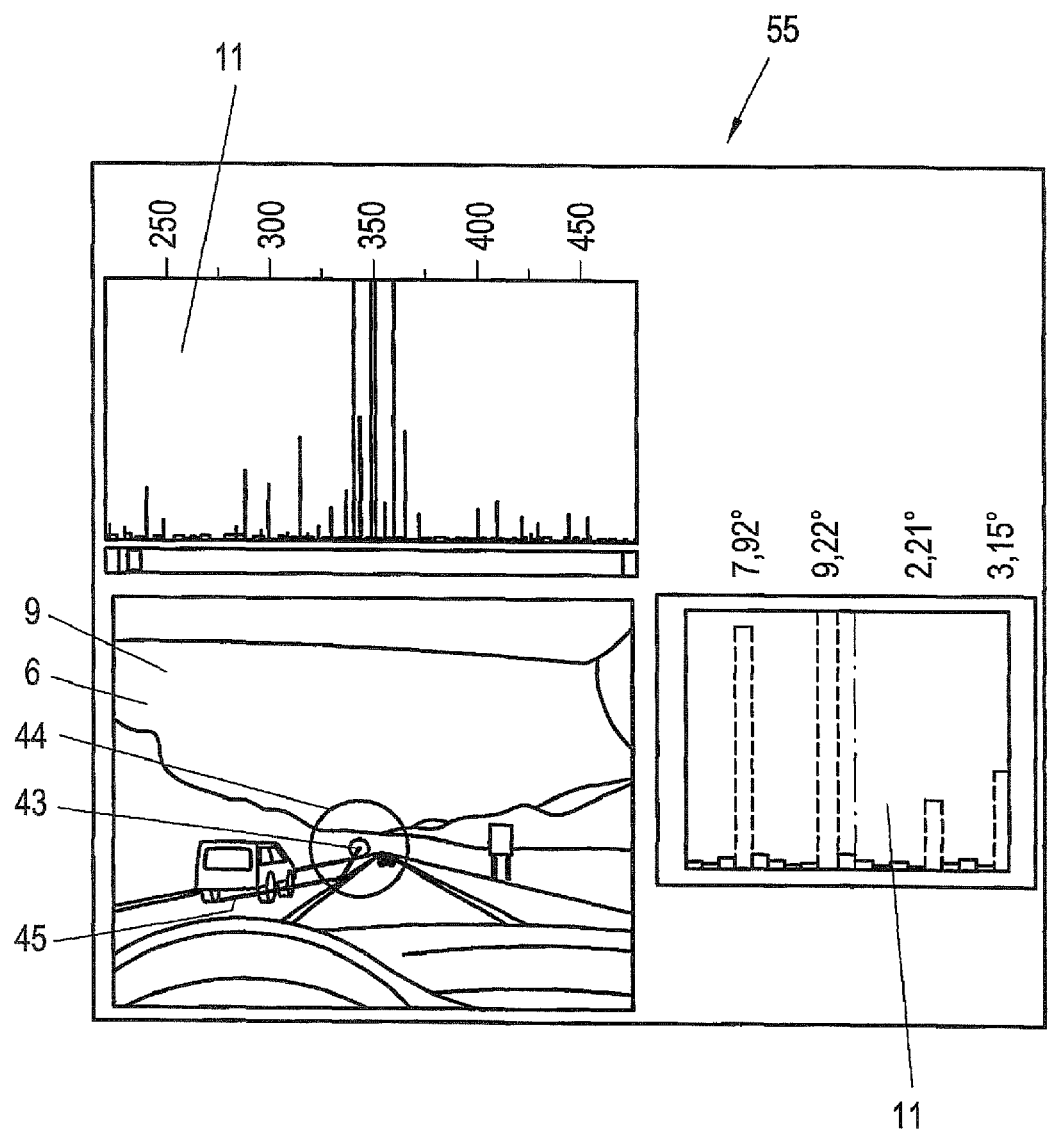
FIG. 12 a preferred user interface for a preferred computer-implemented embodiment of the invention.

FIG. 12 shows a screenshot of a preferred user interface (55) of a computer programme for the execution of a method according to the invention, wherein at the bottom left the visual field image (9) is depicted in which, according to the method described below, point of vision information is output concerning the affiliation of the individual points of vision (37, 38) to a fixation (48, 49) or a saccade. At the top left of the visual field video (9) a first diagram (11) is output (12) in synchronisation to this, wherein to the right of the visual field video (9), also in synchronisation to the image field video (9), a detailed section of the first diagram (11) is output. Moreover, the preferred user interface has a row of control and/or input methods.

Figure 8:
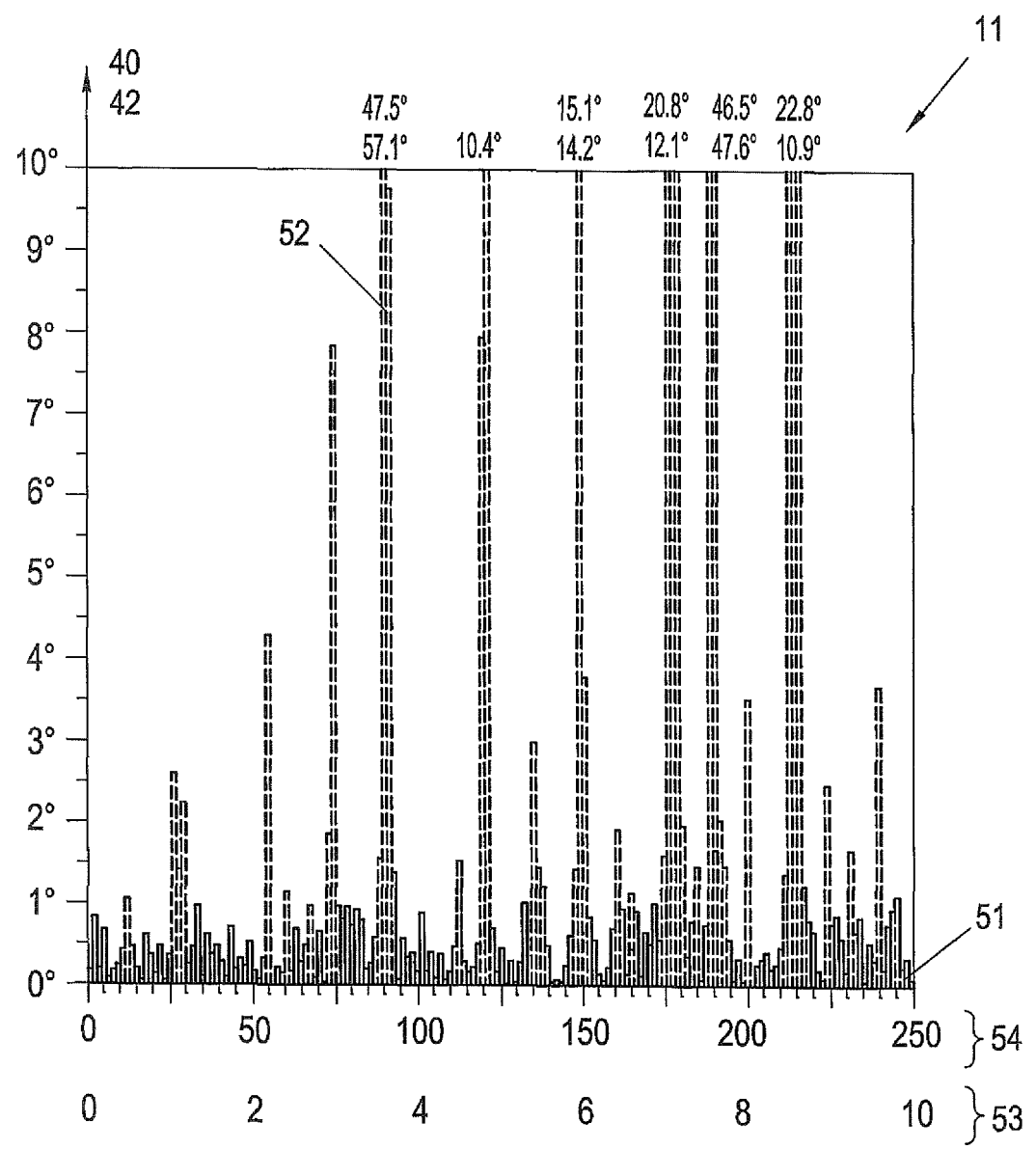
FIG. 8 a preferred embodiment of an output of the first relative distance.

In the first diagram (11) the first relative distance (40) between two following points of vision (37, 38) or between two following points of vision (37, 38), which have been compared in the comparison device with regards to compliance with the first fixation criterion (25), is output during an image field video (9). FIG. 8 shows a preferred embodiment of a first diagram, wherein the time (53) or the sequential number (54) of frames, that is the visual field images, of the visual field video (9) is entered on the x-axis, the first relative distance (40) or the first relative angle (42) is entered on the y-axis. Information regarding whether or not this first relative distance (40) between two following visual field images has been assigned to a saccade or a fixation (48, 49) is also indicated by the colour design or brightness of the individual first relative distances (40) or the first relative angle (42) displayed. Based on this type of first diagram (11), it is quick and easy to check visual field videos (9) for perception, particularly visual awareness. It can also be provided that in the first diagram (11) a marker is displayed to indicate the point currently represented in the visual field video (9), wherein the first diagram (11) is continuously updated with continuous visual field video (9) and/or continuously displayed around the fixed marker as a moveable and changing first diagram (11).

In addition to outputting the data regarding whether a point of vision (37, 38) is assigned to a fixation (48, 49) or a saccade, in the first diagram (11), it can be provided that the corresponding data is output in a specially adapted visual field video (9), as illustrated in FIG. 3 by blocks 6, 7 and 8. Preference is given to three different output types, wherein it can be provided that only one of these output types is output, or it can be provided that two or all three output types are represented at the same time.

FIG. 9 shows a first preferred output type (6), which is also shown in the screenshot in accordance with FIG. 12, wherein together with a point of vision (37) corresponding to the current visual field image displayed in the visual field video (9), a first circle (43) is output uniformly around point of vision (37) with the radius of the fits distance (39), and/or together with a point of vision (37) corresponding to the current visual field image displayed in visual field video (9), a second circle (44) is output uniformly around the point of vision (37) with the radius of a predefinable second distance, wherein the second distance is preferably a second viewing angle, which preferably describes an area (35) assigned to parafoveal vision, particularly with a radius up to 5° and above, wherein when viewing the visual field video (9) the areas can be identified in which ordered or unordered perception is possible due to the distribution of the acuteness of vision around the central optical axis. In addition, it can be provided that by connecting following points of vision (37, 38) first visual traces (45) are determined, which are illustrated at least temporarily in the visual field video (9), therefore, that the visual traces (45) are hidden from visual field video (9), particularly becoming continuously weaker, wherein it is quick and easy to identify which areas of the visual field video (9) are held in the test subject's memory or short-term memory during a short period depending on the person.

A second preferred output type (7) is illustrated in FIG. 10, wherein it is provided that the points of vision (37) corresponding to the first fixation (48) at least are surrounded uniformly by a third circle (46), wherein the radius of the third circle (46) is a function of the continuous duration of the first fixation (48), therefore the third circle becomes increasingly larger as the duration of the respective fixation continues. In addition, it can be provided that the saccades between two following fixations (48, 49) are connected via the points of vision by a line. It is preferred that the individual fixations (48, 49) or saccades shown after a predefinable time are hidden again from the visual field video (9). To ensure that a distinction can be made between several saccades or fixations (48, 49) that are output at the same time, it can be provided that these are marked with different colours and/or grayscales, wherein it can be provided that the sequence of fixations is indicated by different colours, grayscales and/or formation of the circles.

FIG. 11 shows a third preferred output type (8) of the output of the visual field video (9), wherein it is provided that this is shaded and the point of vision (37) corresponding at least to the first fixation (48) is shown surrounded uniformly by a fourth circle (47) in principle, wherein the area of the fourth circle (47) is shown lighter, at least temporarily, compared to the shaded visual field video (9). This represents a particularly advantageous design, in the form of a spotlight or a searchlight, as only areas that are output visibly are or have been actually perceived by the observed. All other areas are shaded, because these have not actually been perceived.

In addition to the output of the visual field video (9) processed according to the invention or to the output (12) of the first diagram (11) (FIG. 8) an evaluation of the entire sequence of a predefinable first section or the entire visual field video (9) can be provided, wherein a selection (13) (FIG. 3) of a first section of the visual field video (9) can be provided. In an evaluation unit (14) all of the following points of vision (37, 38, 69, 70) that satisfy the first fixation criterion (25), together assigned to a first fixation (48), the angular distance between the first point of vision (37) assigned to the first fixation (48) and the last point of vision (70) assigned to the first fixation (48) is determined and output as the first fixation angle (51) (FIG. 13). In addition, it is preferred that the angular distance between the last point of vision (70) assigned to the first fixation (48) and a first point of vision (73) assigned to a second fixation (49) is determined and output as the first saccade angle (52) (FIG. 14). As a result, it is possible to accurately measure the attention for specific predefinable objects or scenes of a visual field video (9), as in addition to the first measured result, therefore whether or not a point of vision (37) is assigned to a fixation (48) or a saccade, a second measured result is also determined over the duration or local length of the fixation (48) or the saccade. It is preferred that for a predefinable first section of the visual field video (9), the frequency of the determined fixations (48, 49) are output depending on the fixation angle (51), and/or that the frequency of the saccades determined for the first section of the visual field video (9) are output depending on the saccade angle (52) or the time. It is preferred that the fixations (48, 49) satisfy the first fixation criterion (25) or these are output in a first fixation diagram (15) and that the saccades determined for the first fixation criterion (25) are output in a first saccade diagram (20). This enables an entire sequence or a predefinable first section to be assessed simply and quickly. FIG. 13 shows such a first fixation diagram (15), wherein the first fixation angle (51) is entered on the x-axis and the frequency (56) with which the fixations (48, 49) occur with the respective fixation angle (51) are entered on the y-axis. The first fixation diagram (15) shown in FIG. 13 shows the changes in fixation during a car journey. FIG. 14 shows a corresponding first saccade diagram (20), wherein the first saccade angle (52) is entered on the x-axis and the frequency (56) with which the saccades occur with the respective saccade angle (52) are entered on the y-axis. The first saccade diagram (20) shown in FIG. 14 shows the changes in saccade during a car journey. It is preferred that the user interface offers a means for selecting a first section of the visual field video (9).

It can also be provided that the first section in the form of a window of predefinable size is formed on both sides of the marker shown in the first diagram (11) and that the first fixation diagram (15) and/or the first saccade diagram (20) generates and displays a constant length for this first section but a continuously changing content.

Figure 30:
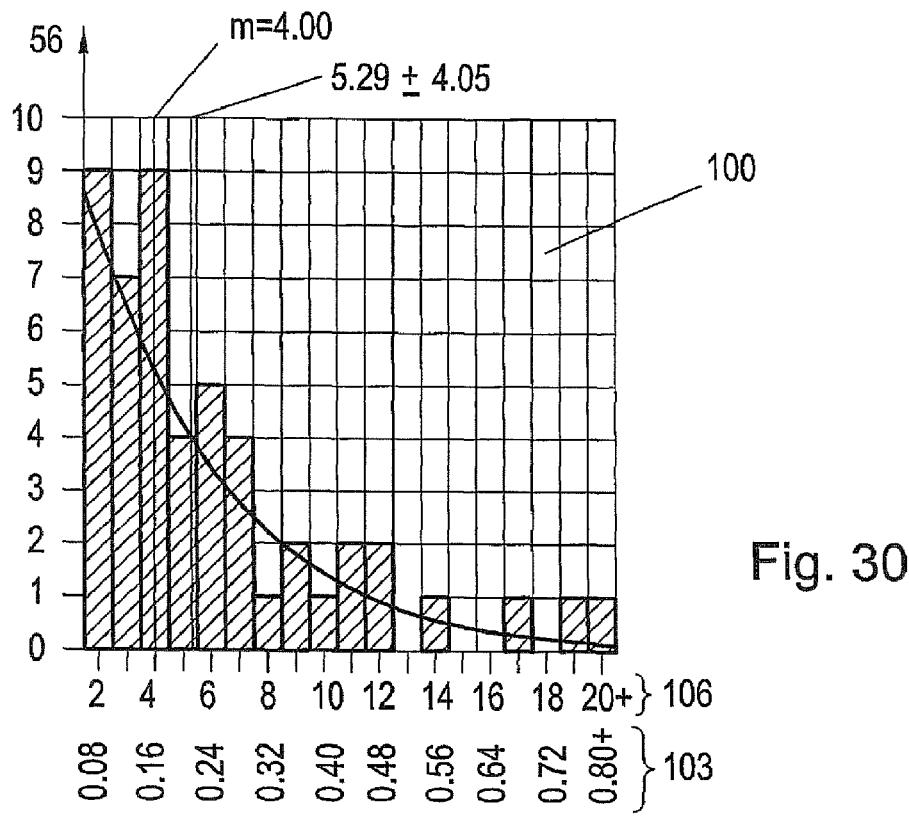
FIG. 30 a first preferred output of the frequency of the fixations determined depending on the fixation duration.

In addition or alternatively to the output of the first fixation diagram (15) and/or the first saccade diagram (20), it is preferred that for a predefinable section of the visual field video (9) all of the following points of vision (37, 38, 69, 70), which each satisfy the first fixation criterion (25), together assigned to a first fixation (48), and that a first fixation length (103) is determined between the first point of vision (37) assigned to the first fixation (48) and the last point of vision (70) assigned to the first fixation (48) and that the frequency (56) of the determined fixations (48, 49) are output depending on the first fixation length (103). FIG. 30 shows a preferred output type in the form of a fixation length diagram (100), wherein the first fixation length (103) is entered on the x-axis as the duration of a fixation (48, 49), wherein the number of frames (106) or the images of a visual field video (9) can be stipulated as equivalent scaling, and wherein the frequency (56) with which fixations (48, 49) occur with the respective fixation length (103) in the predefinable first section of the visual field video (9) is entered on the y-axis.

Figure 31:
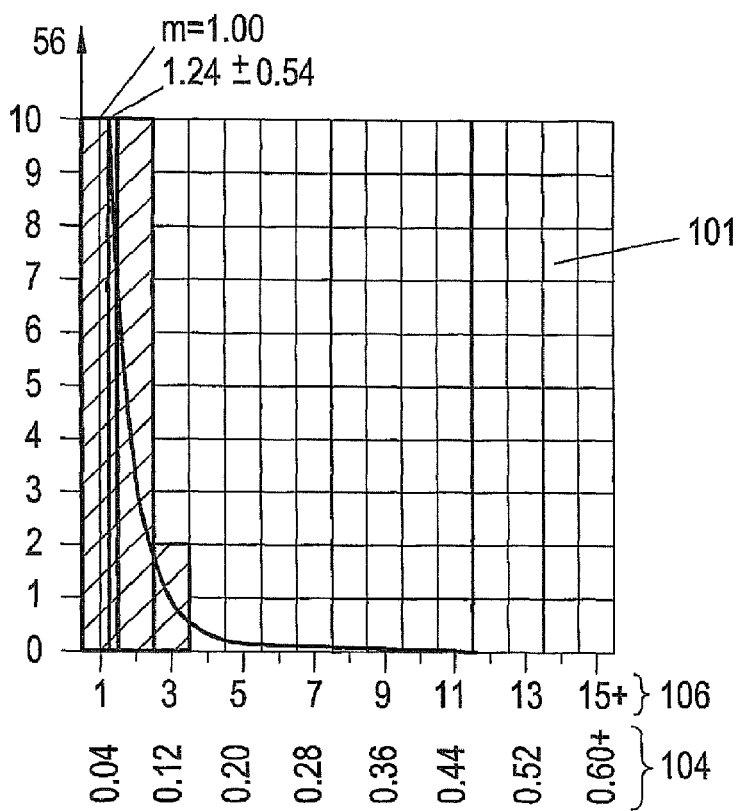
FIG. 31 a first preferred output of the frequency of the saccades determined depending on the length of saccade.

Furthermore, it is in particular preferred that for the first section of the visual field video (9), a first saccade length (104) between the last point of vision (70) assigned to the first fixation (48) and a first point of vision (73) assigned to a second fixation (49), and that the frequency (56) of the determined saccades are output depending on the first saccade length (104). FIG. 31 shows a preferred output type in the form of a saccade length diagram (101), wherein the first saccade length (104) is entered on the x-axis as the duration of a saccade, wherein the number of frames (106) or the images of a visual field video (9) can be stipulated as equivalent scaling, and wherein the frequency (56) with which saccades occur with the respective saccade length (104) in the predefinable first section of the visual field video (9) is entered on the y-axis. By outputting the frequency (56) at which the saccades or fixations (48, 49) occur depending on the first saccade length (104) or the first fixation length (103), it is possible to quickly and easily analyse that type and quality of attention in the first section. This allows object-based and/or situation-based differences to be identified quickly and easily.

Figure 32:
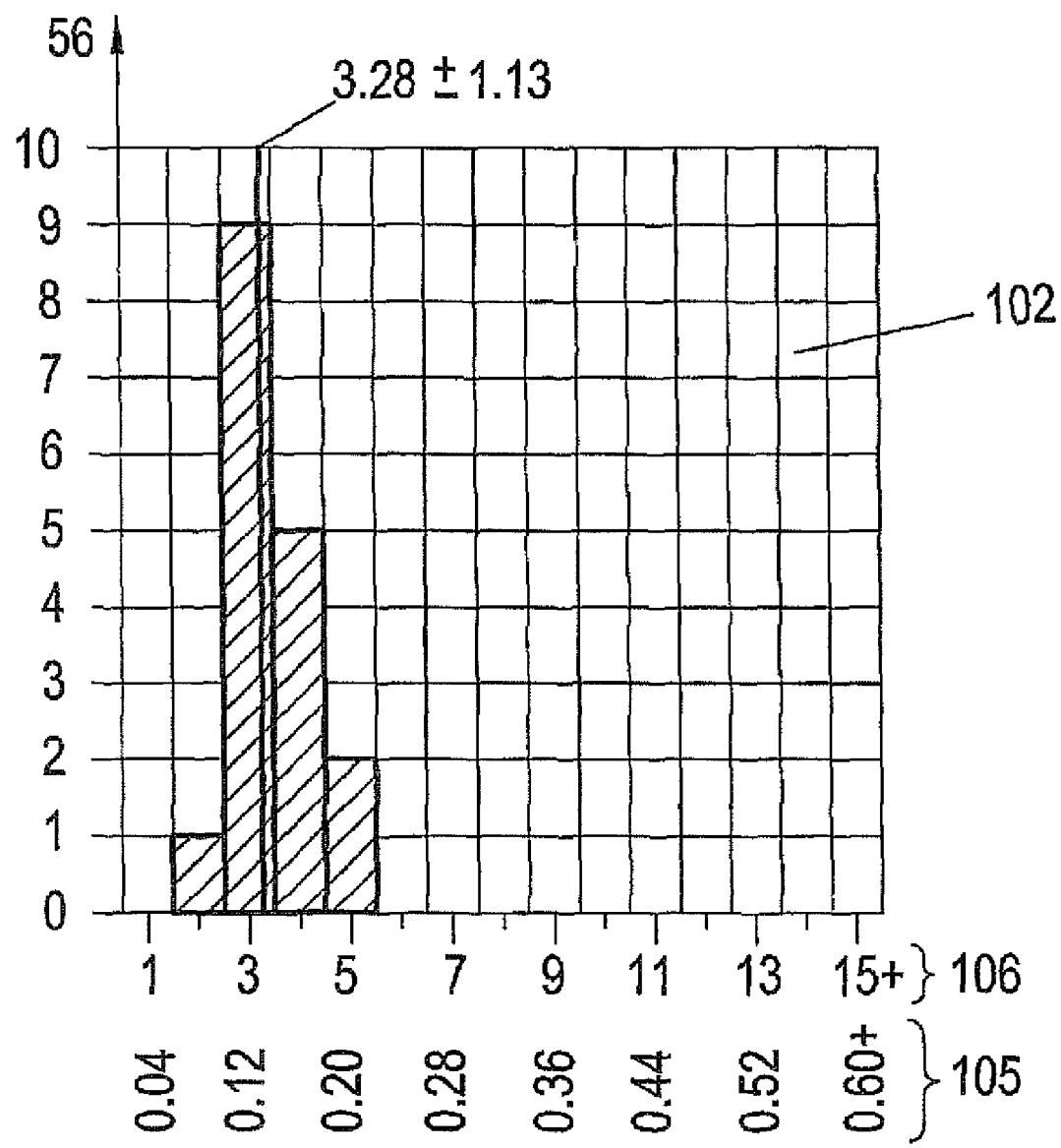
FIG. 32 a first preferred output of the frequency of the blinks counted depending on the length of blinking.

In the method according to the invention, periods of time during which the test subject's eyes are closed can also be identified automatically. This period of time is triggered by a blink during which the pupil is covered temporarily by the eyelid. It has been determined that it is useful to test the first blink length (105) when analysing the physiological connections as the length of a blink and the frequency with which blinks of a predefinable first blink length (105) occur. FIG. 32 shows a preferred output type as a blink diagram (102), wherein the frequency (56) at which blinks of a predefinable first blink length (105) occur is output. It has been shown that based on the low frequency of blinks or the first blink length (105), a high degree of complexity of situation or an object can be concluded and vice versa. In addition, a reduced blink frequency can result in the eye drying out and ultimately in eye and/or visual problems. From the above description it can therefore be concluded that a reduction in visual capacity can be expected based on the decrease blink frequency.

In addition, in the method according to FIG. 3 there are further options for assessing the determined data, such as other output methods (64, 65, 66, 67, 68, 87, 88, 89, 90) which are explained in detail elsewhere. Moreover, it can be provided that the first fixation criterion (25) is replaced with a second fixation criterion (26) and thereby at least one predefinable second section of the visual field video (9) is retested to determine how this is illustrated by the dashed line between the selection (13) of the predefinable first or section of the visual field video (9) and the first fixation criterion (25).

As illustrated above, and based on a definition of the foveal area (34) as the area in which ordered perception is possible, the first viewing angle (41) of the foveal area (34) depends significantly on the object or surroundings. For example, known objects in a surroundings in which the test subject expects this object to appear (such as an octagonal stop sign in road traffic) are very quickly received or detected by the test subject. Unexpected or unknown objects, on the contrary, are not detected or perceived as quickly or as uniquely.

Figure 4:
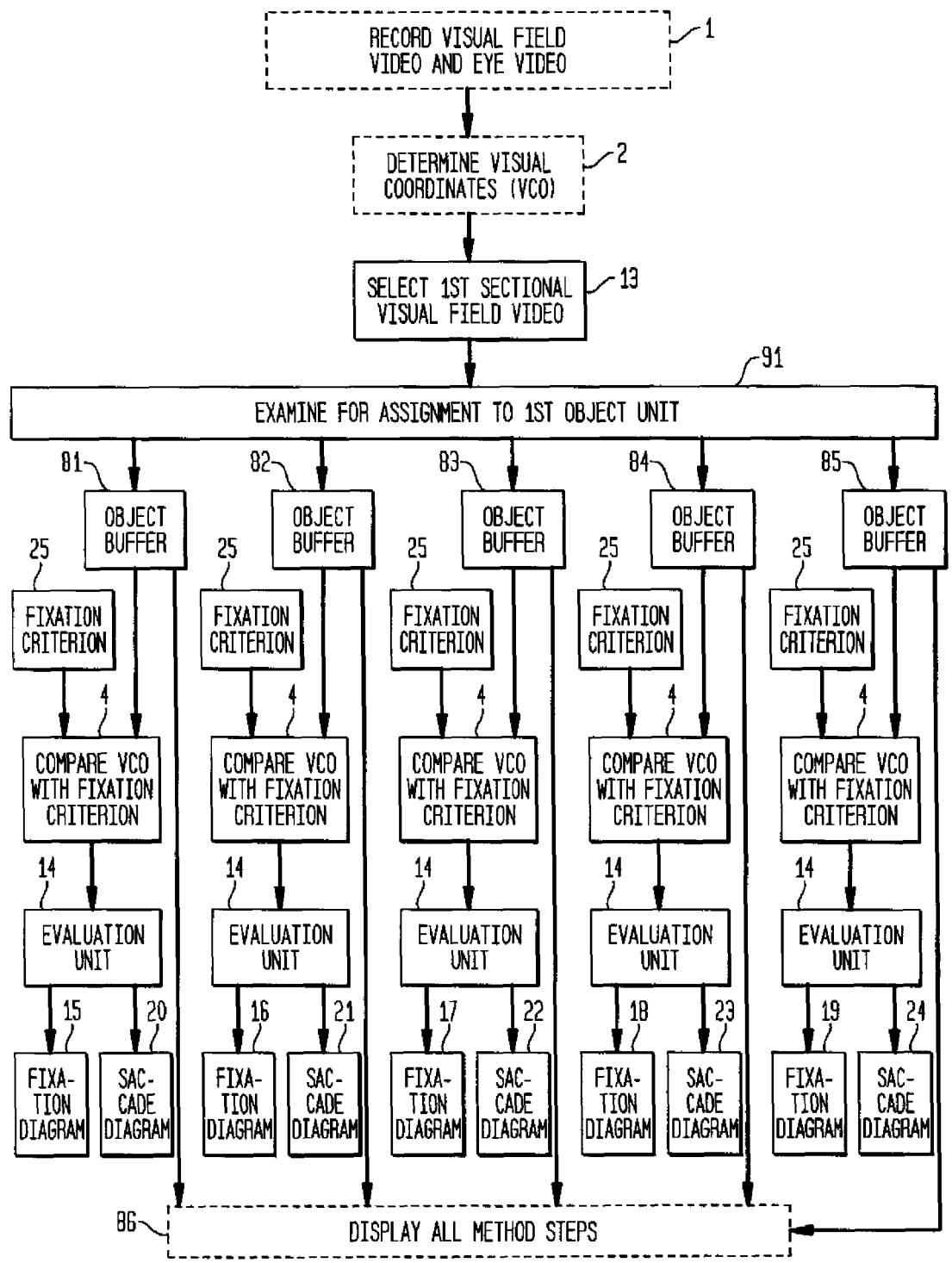
FIG. 4 a block diagram of a third embodiment of the invention.
Figure 5:
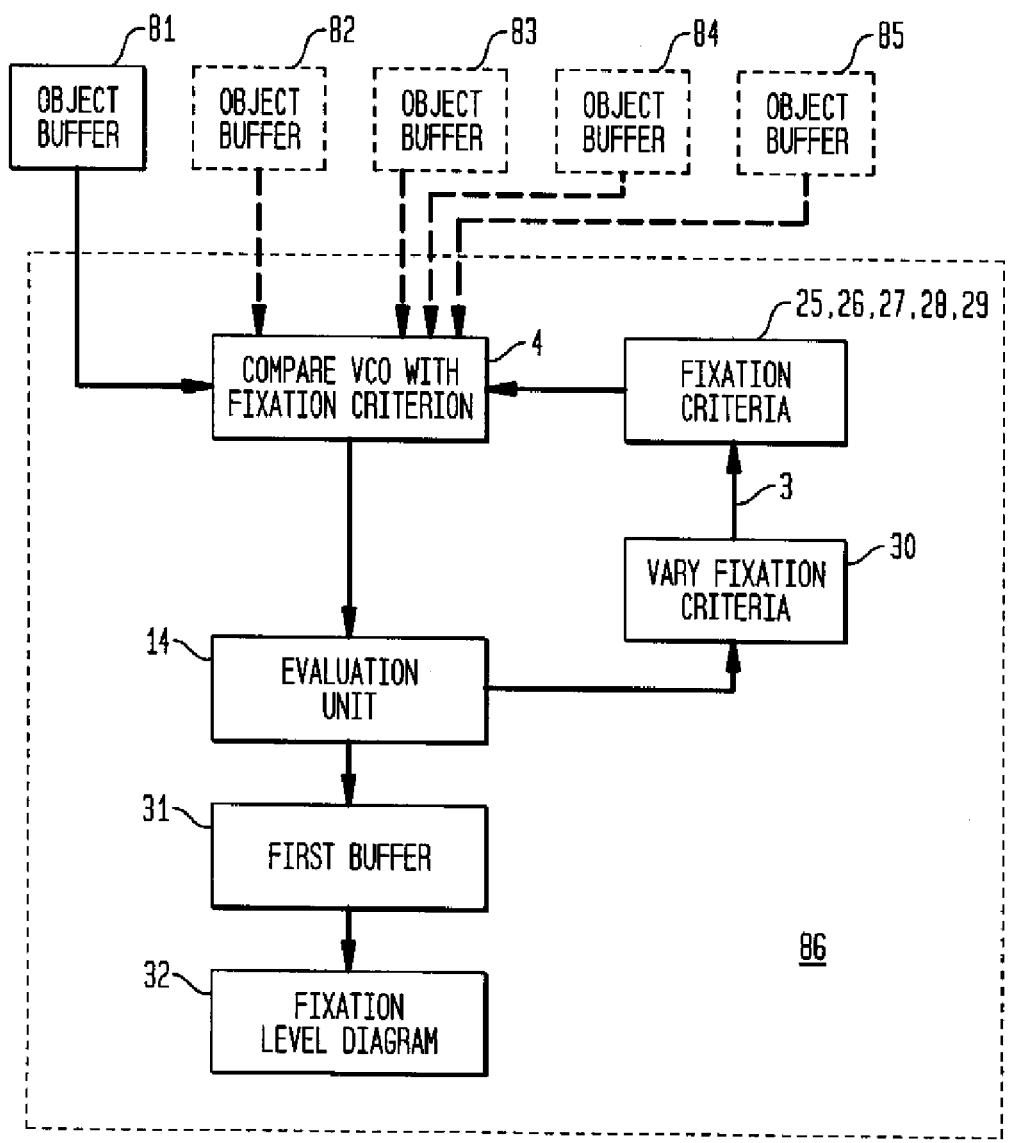
FIG. 5 a block diagram of a fourth embodiment of the invention.

Method for measuring the perceptibility of predefinable object units, wherein for a predefinable third section of the visual field video (9) all of the points of vision assigned to a predefinable first object unit are collected in a first object buffer (81) and that the method described above is carried out with the points of view collected in the first object buffer (81). Consequently, at least one object unit is selected for a predefinable or selectable third section of the visual field video (9), preferably a predefinable number of object units is selected, for example such as in FIGS. 4 and 5 shown with five object units. The selection of object units is preferably carried out by a user, wherein however at least one object unit is selected automatically. For example, the first object unit can be a stop sign, the second object unit can be a car and the third object unit can be the lane separator on a road. An objective unit within the meaning of this invention can also be a scene of the visual field video such as travelling round a bend.

FIG. 4 shows a method in which after selection (13) a third section of the visual field video (9), this third section of the visual field video (9) is tested for points of vision, which are assigned or have been assigned to the predefined object units. Points of vision to be assigned or already assigned as a first object unit refers to all points of vision that occur between the first point of vision of a first fixation concerning the first object unit and the last point of vision of a last fixation concerning the first object unit in the third section of the visual field video. After the selection (13) of the third section of the visual field video (9), this is examined (block 91) for aspects that are assigned or have already been assigned to the first object unit. This examination and assignment of individual points of vision to individual object units can be carried out manually by a user or automatically using a computer, for example with software for the automatic detection of predefinable optical patterns, such as stop signs, road markings, people and so on.

The points of vision stored in the individual object buffers (81, 82, 83, 84, 85) are then, as shown in FIG. 4, processed and analysed using the method described above. After the analysis, a fixation diagram (15, 16, 17, 18, 19) and a saccade diagram (20, 21, 22, 23, 24) are output for each object buffer. Therefore in the preferred method according to FIG. 4 a preferred first fixation diagram (15), a second fixation diagram (16), a third fixation diagram (17), a fourth fixation diagram (18) and a fifth fixation diagram (19) is output, as well as a first saccade diagram (20), a second saccade diagram (21), a third saccade diagram (22), a fourth saccade diagram (23) and a fifth saccade diagram (24). It is thus possible to distinguish and evaluate possible different objects in terms of their quality of perception. In particular, it is possible to assign a so-called request characteristic to various possible objects in regard to how strong a persons attention is drawn to the object in question. Consequently, there are objects that attract the attention of the observer because of their design, wherein other objects fail to attract the attention of the observer. The understanding of how an object must be designed in order to attract attention or which objects attract attention by the observer is important in many areas of everyday life, such as in the design of pedestrian crossings, safety clothing, road layouts or advertising media. In addition, in the method according to FIG. 4 there are further options for assessing the determined data, such as other output methods (64, 65, 66, 67, 68, 87, 88, 89, 90) which are explained in detail elsewhere.

Known or expected objects are recognised fully as such from the furthest first viewing angle (41) before unknown or unexpected objects. As a result, the acuteness of vision and thus also the foveal area (34) for a first object or first surroundings can be larger or smaller than for a second object or second surroundings. The size of the acuteness of vision required for the specific object therefore represents an extremely meaningful value for the perception of an object or a scenic sequence, wherein the term scenic sequence can relate to all chronologies, such as passing a road or viewing an advertisement.

The larger the area around the central optical axis in or for which an object is detected, the quicker and easier this is perceived by an observer and the higher the probability that this is also perceived correctly by the observer as such an object, even if the first fixation criterion (25) is not satisfied for adjacent objects. For example, an observer could recognise the advertisements affixed to the roof for a known soft drinks firm or a known fast-food chain when paying a fleeting glance over a building, whilst the shape of the roof itself is not perceived.

The invention therefore relates to a method for measuring the perception of predefinable object units, wherein the method described above is carried out for at least one predefinable second section of the visual field video (9) with at least one predefinable second fixation criterion (26) that differs from first fixation criterion (25), wherein the quality of predefinable objects and/or glance sequences can be determined in terms of their perceptibility by an observer. FIG. 5 shows a preferred embodiment of such a method as a block diagram, wherein the individual steps of the method are shown together as a joint dotdashed block (86). In a preferred embodiment of the invention it is provided that the second area is identical to the third area, wherein it is particularly preferred that corresponding methods summarised in block 86 apply to the points of vision to be assigned or already assigned to a predefinable first object unit stored or collected in the first object buffer (81), as represented in FIG. 5.

In the embodiment according to FIG. 5 it is provided that the second section of the visual field video (9) or the content of the first object buffer (81), the second object buffer (82), the third object buffer (83), the fourth object buffer (84) and/or the fifth object buffer (85), is processed in series one after the other in the comparison device (4) and the evaluation (14) each with different fixation criteria (25, 26, 27, 28, 29), therefore one after the other at least with a first fixation criterion (25), a second fixation criterion (26), a third fixation criterion (27), a fourth fixation criterion (28) and a fifth fixation criterion (29), in the form of a process loop (30) to vary the fixation criterion, wherein the results of a first buffer (31) are stored and then output.

Figure 15:
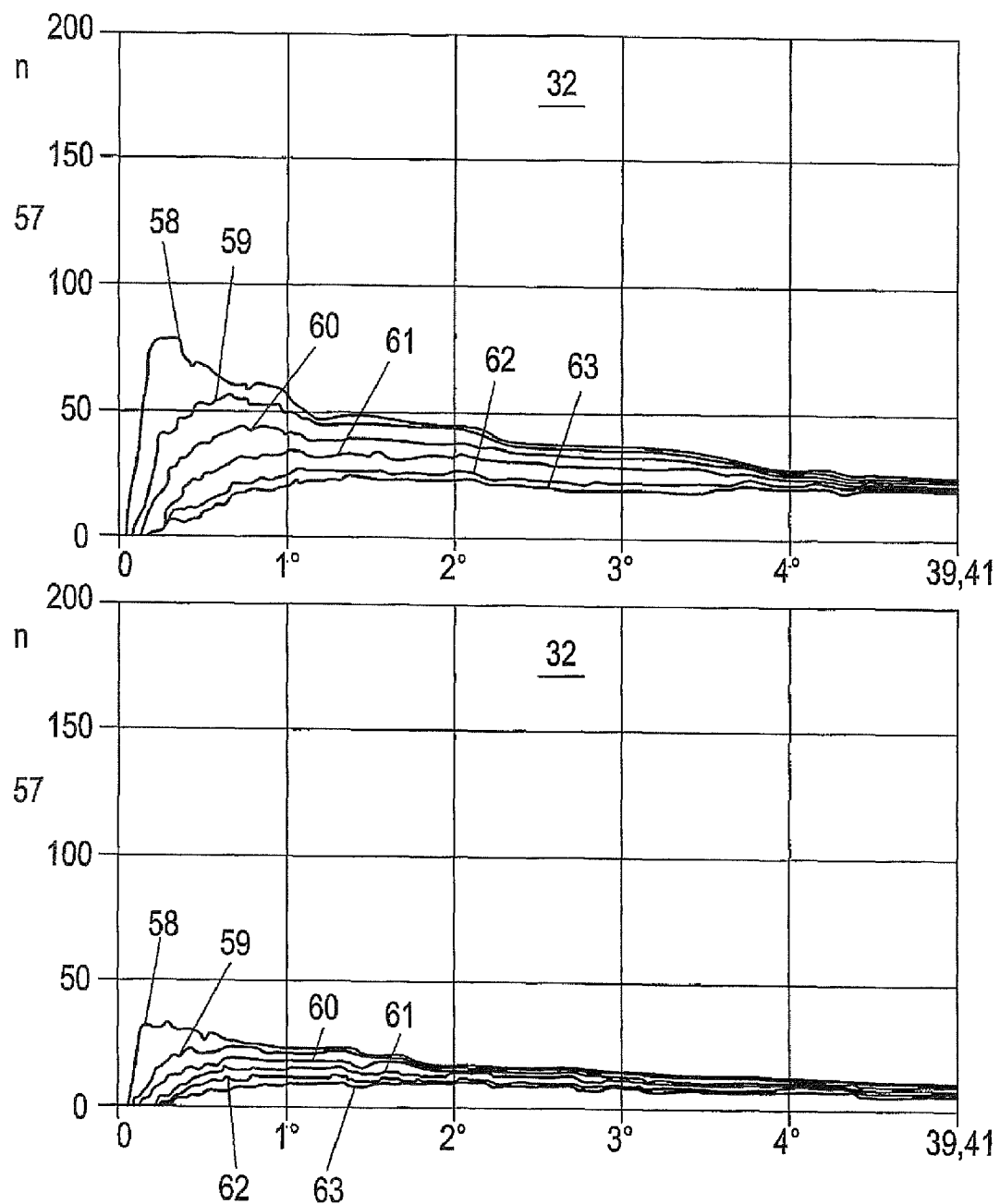
FIG. 15 a first preferred output of the frequency of the fixations depending on the variable fixation criterion as a set of curves with constant initial duration.

It is preferred that the data determined concerning object perception dependent on the respective fixation criterion (25, 26, 27, 28, 29) is output. It is preferred that the frequency of fixations (48, 49) is output depending at least on the first and the second fixation criterion (25, 26) as the first curve (58) with constant first duration and as second curve (59) with constant second duration. FIG. 15 shows such a second diagram, which is referred to as such a fixation level diagram (32), in which the first distance (39) or the first viewing angle (41) is entered on the x-axis and the number (57) of fixation is entered on the y-axis, and wherein each of the six curves (58, 59, 60, 61, 62, 63) displayed has been determined with different first durations, therefore for the first curve (58) the distance between the first visual field image (37) and the second visual field image (38) is a frame or a visual field image, therefore the second visual field image (38) is the visual field image directly following the first visual field image (37). In the second curve (59), the distance between the first visual field image (37) and the second visual field image (38) is two frames. In the third curve (60), the distance between the first visual field image (37) and the second visual field image (38) is three frames. In the fourth curve (61), the distance between the first visual field image (37) and the second visual field image (38) is four frames. In the fifth curve (62), the distance between the first visual field image (37) and the second visual field image (38) is five frames. In the sixth curve (63), the distance between the first visual field image (38) and the second visual field image (38) is six frames. FIG. 15 shows two different fixation level diagrams (32), which each concern different scenes or objects. These fixation level diagrams (32) can be used to quickly determine differences that are specific to perception in different objects depending on the first distance (39) or the first viewing angle (41) and the first duration, wherein a scientific evaluation or measurement of the different perceptibility of objects is enabled. It is therefore possible to assign a so-called request characteristic to various possible objects in regard to how strong a person's attention is drawn to the object in question.

For further evaluation and analysis of the eye glance behaviour and the object perception, as already explained above, other output formats can be provided, as illustrated in FIGS. 16 to 20, and 24 to 27.

Figure 16:
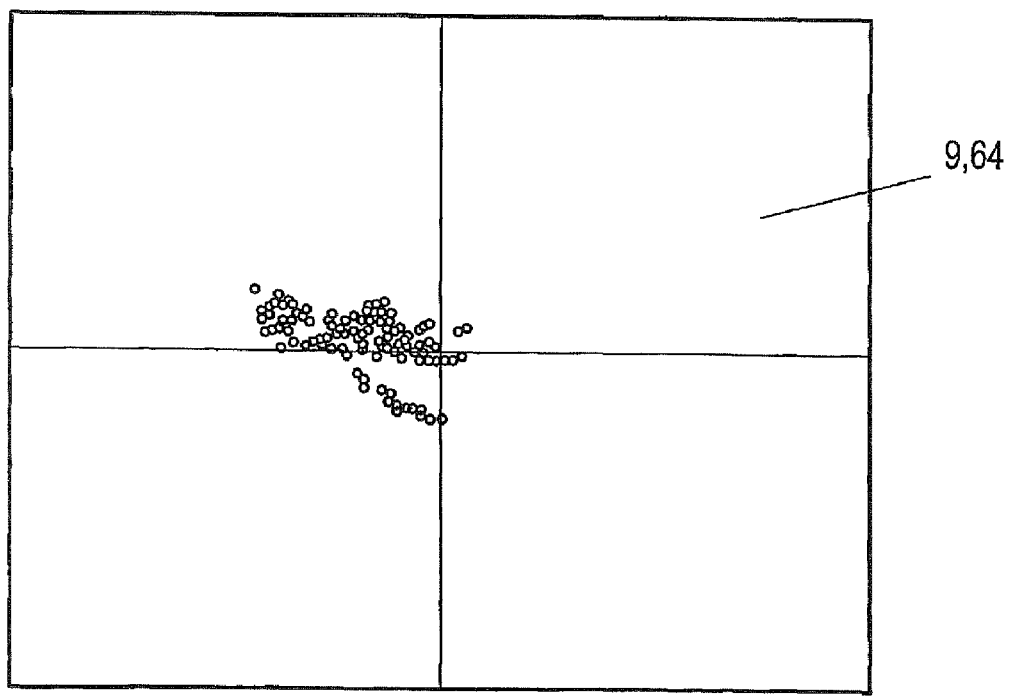
FIG. 16 a fourth preferred output of a visual field video.

FIG. 16 presents all points of vision for a first object unit, therefore all of the points of vision stored in the first object buffer are represented without any special evaluation and/or weighting. Such a representation, also referred to as "Dots" (64), allows a practised observer to make a series of statements regarding the quality of the observed object. The greyed out area can, both in its method of representation as well as in all further methods of representation in accordance with FIGS. 16 to 20, as well as 24 to 27—also include an image of the first object in the background for ease of understanding, where it must be considered that during dynamic approximation, the points of vision represented do not have to be targeted at the areas represented in the stored image.

Figure 18:
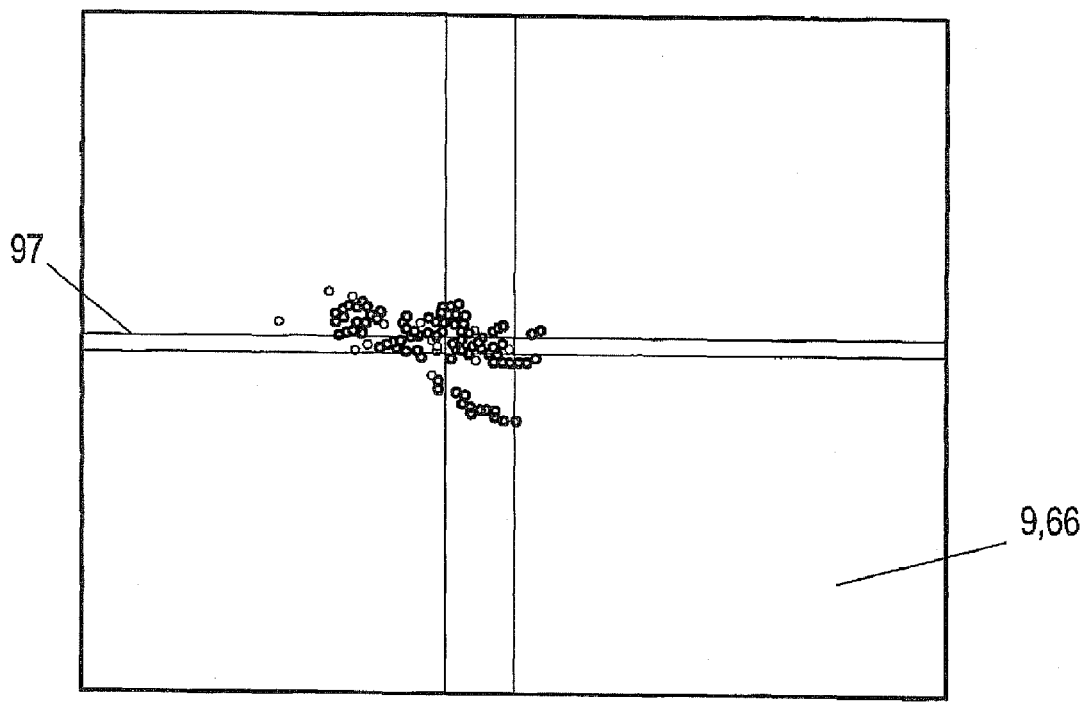
FIG. 18 a sixth preferred output of a visual field video.

FIG. 18 shows all points of vision preferred for a first object unit, therefore all of the points of vision stored in the first object buffer are represented, wherein all points of vision assigned to a fixation are labelled, wherein it is preferred that these are represented compared to the surroundings in a highly perceivable contrast and/or in a highly perceivable difference in brightness and/or in a different colour to the surroundings. The points of vision represented and output in this manner are also referred to as fixed dots (66). As a result, it is possible to evaluate the quality of perception of a first object accurately and in greater detail. FIG. 18 also represents a first axis system (97), which marks the centre point and/or focus of the points of vision.

Figure 19:
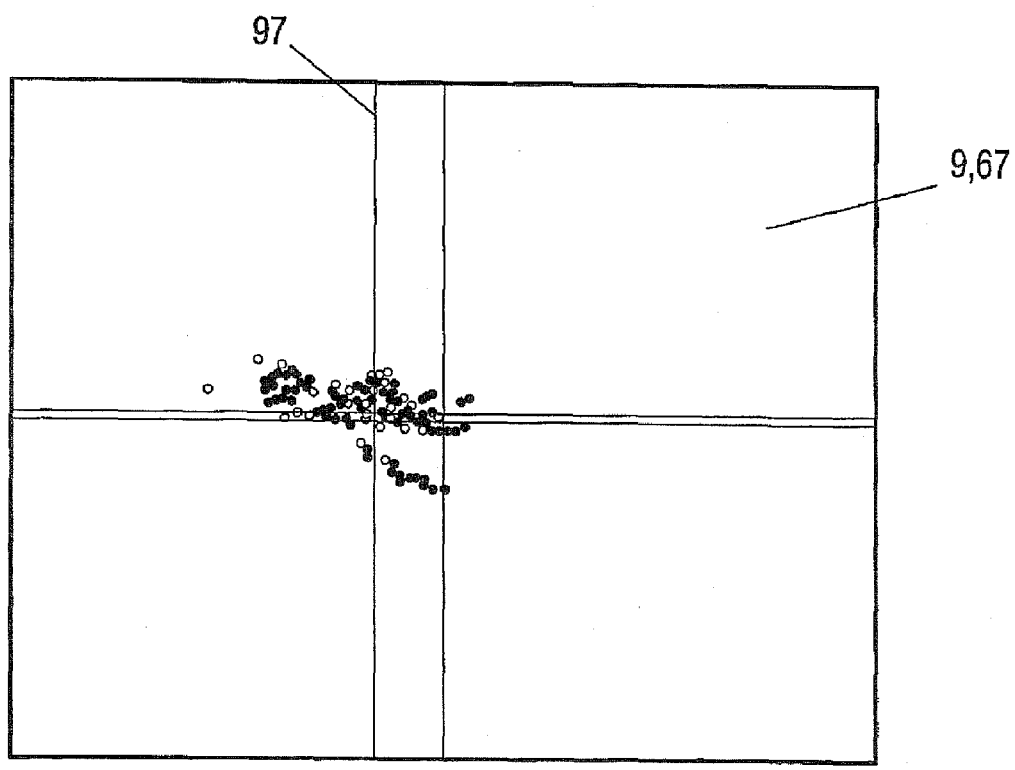
FIG. 19 a seventh preferred output of a visual field video.

FIG. 19 also shows all points of vision in the object memory, with all points of vision associated with a fixation of predetermined length marked, whereby it is preferred that provision is made to ensure that these are shown in easily perceptible contrast against the surroundings and/or in an easily perceptible brightness difference and/or in a colour that is different from the surroundings. The points of vision shown or displayed thus marked are also called "weighted dots" (67). By changing the predetermined length of the fixation, it can be quickly and easily analysed how the quality of perception of an initial object changes depending on the length of the individual fixations. FIG. 19 also shows the first axis intersection (97).

Figure 20:
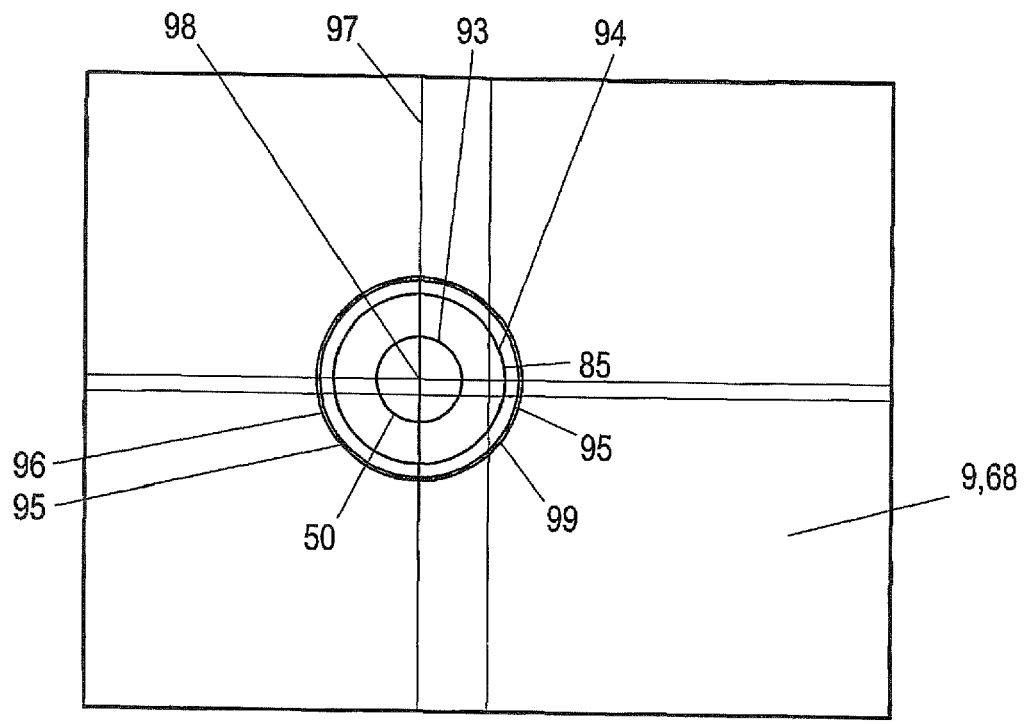
FIG. 20 an eight preferred output of a visual field video.

FIG. 20 shows a preferred output form which can be used in addition to the output forms described elsewhere. Here, a predetermined number of circles are marked around the centre (98) of the fixation points of the first axis intersection (97). It is preferred that a seventh circle (93) is shown, as illustrated, the diameter of which is formed so that the seventh circle (93) includes fifty percent of the points of vision. A further, eighth circle (94) is shown, the diameter of which is formed so that the seventh circle (93) includes fifty-eight percent of the points of vision. A further, ninth circle (95) is shown, so that it includes fifty-nine percent of the points of vision and a tenth circle (96) to show ninety-nine percent of the points of vision. This representation—also called "zone angle" (68)—can be combined with any of the other output forms and enables a quick, object-specific evaluation of the quality of perception.

Figure 17:
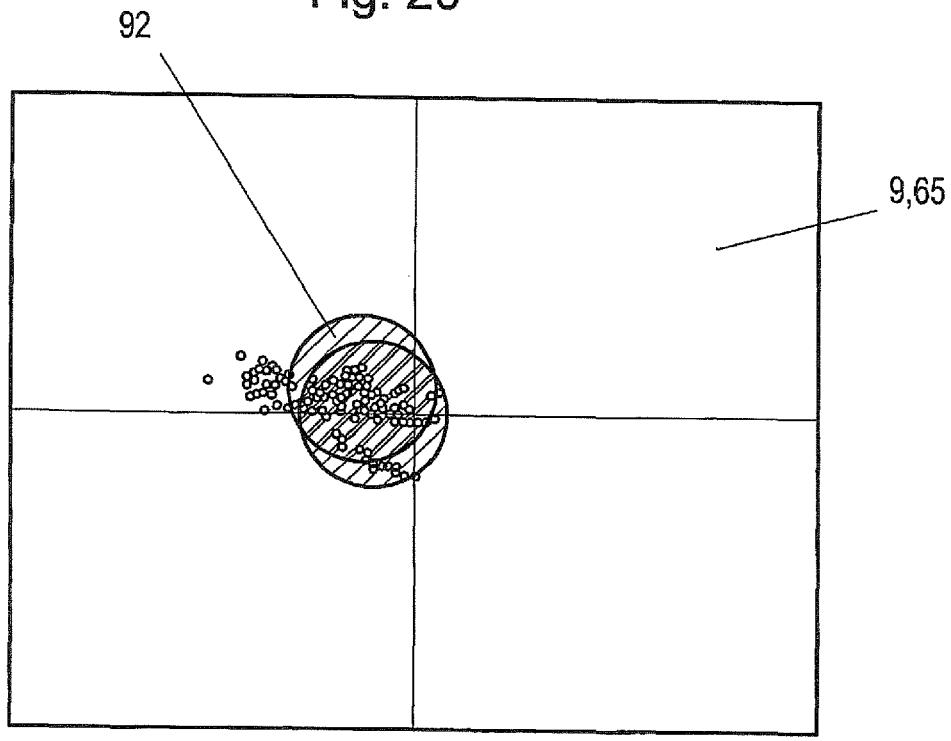
FIG. 17 a fifth preferred output of a visual field video.

FIG. 17, similarly to FIG. 16, shows the points of vision set out in the first object cache, whereby those areas assigned to a fixation after one of these previous "long" saccades are shown by a sixth circle (92), the surface of which is shown in easily perceptible contrast against the surroundings and/or in an easily perceptible brightness difference and/or in a colour that is different from the surroundings. The centre point of the sixth circle (92) is obtained from the centre of the points of vision assigned to the relevant fixation. This form of representation is also called the "fixation dominance" (65). The length of a long saccade is obtained via a predetermined initial saccade angle (52). Alternatively a saccade time period may also be set; a saccade that exceeds this is a long saccade. The diameter of the sixth circle is predeterminable and is preferably located in an area that preferably describes an area related to parafoveal seeing (35). This representation enables a quick, strong impression to be gained of which areas of an object attract particular attention from an observer, even in the case of an unpractised observer. It is also possible to predetermine that the sixth circle (92) will only be shown if the characteristics of fixation (48), (49) and fixation length (103), necessary for the recognition of an object by the observer, are satisfied. This means it will be seen quickly and clearly whether an object has merely been seen in passing, or has been perceived or actually recognised by an observer.

Figure 25:
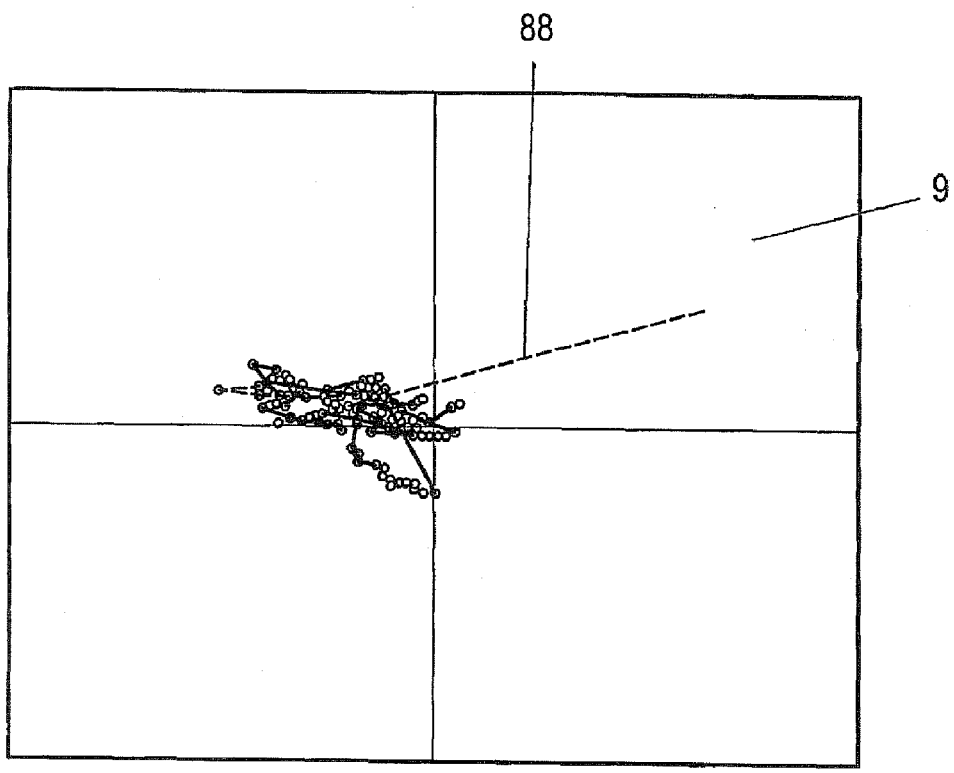
FIG. 25 a tenth preferred output of a visual field video.

FIG. 25 shows a tenth preferred output 88, whereby only the saccades between individual fixations are shown, with the last point of vision of a first fixation being connected by a line with the first point of vision of a second fixation; the length of the saccade may be shown in a different colour, so that an observer can quickly determine the areas with long perception deficits.

Figure 24:
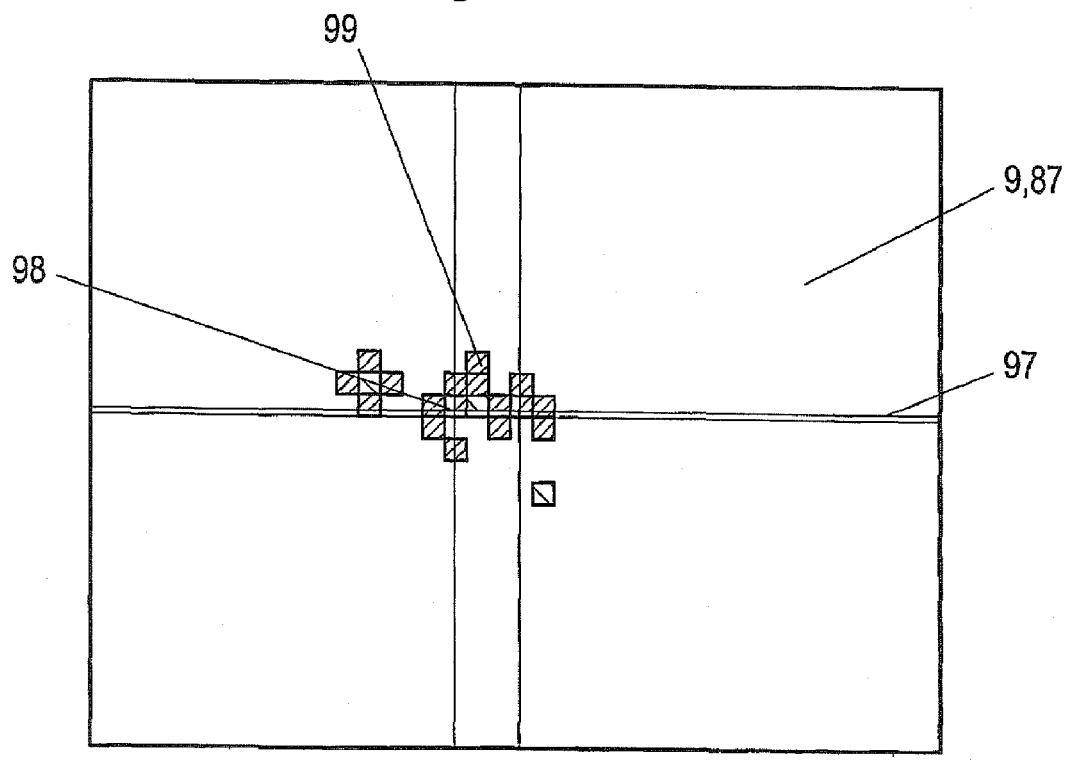
FIG. 24 a ninth preferred output of a visual field video.

FIG. 24 shows a ninth preferred output (87), in which the field of vision is overlaid with a grid of predetermined dimensions and/or arrangement, and the individual grid segments (99) are marked with regard to the frequency of the points of vision occurring therein by a predetermined configuration of brightness, colour and/or shading.

Figure 26:
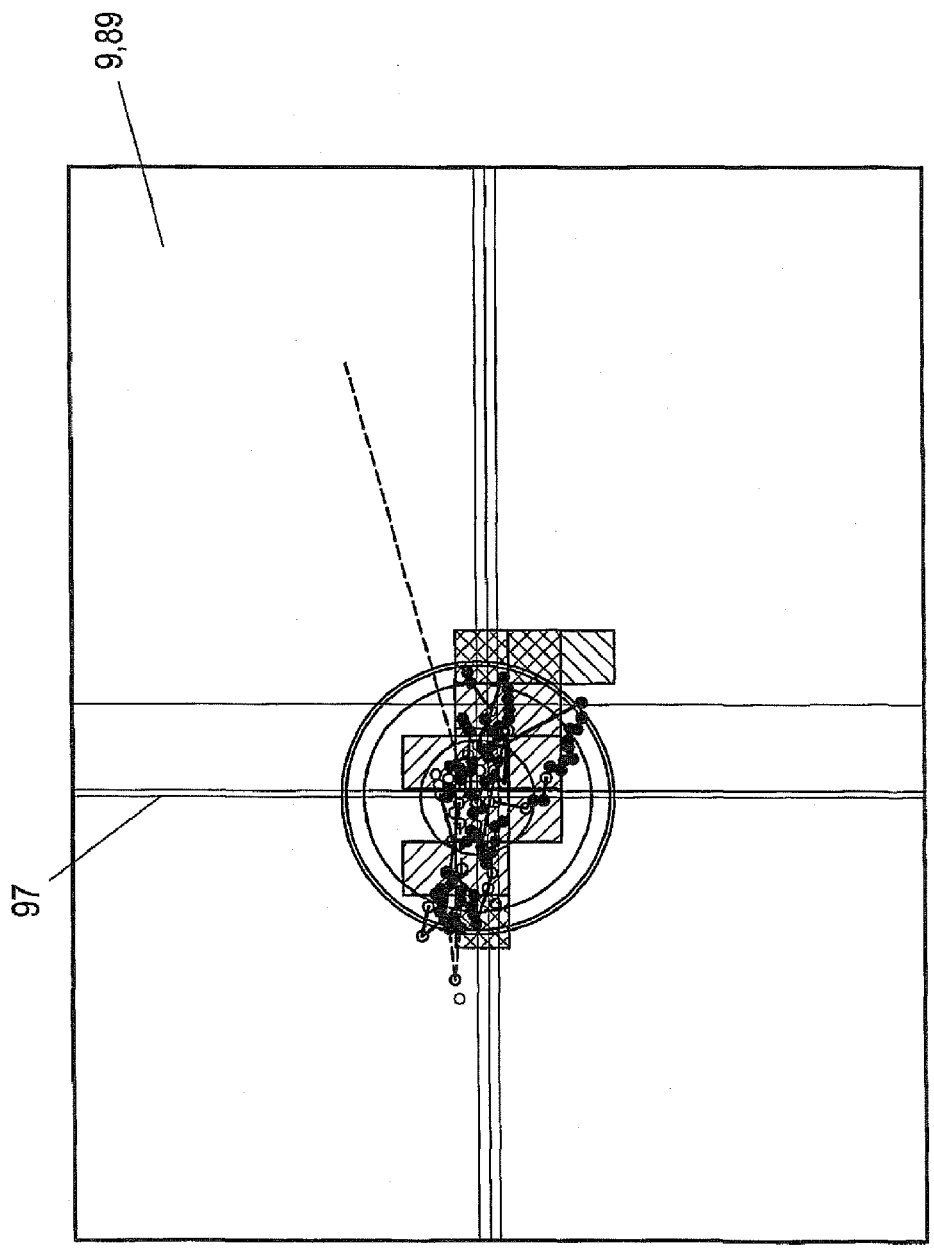
FIG. 26 an eleventh preferred output of a visual field video.
Figure 27:
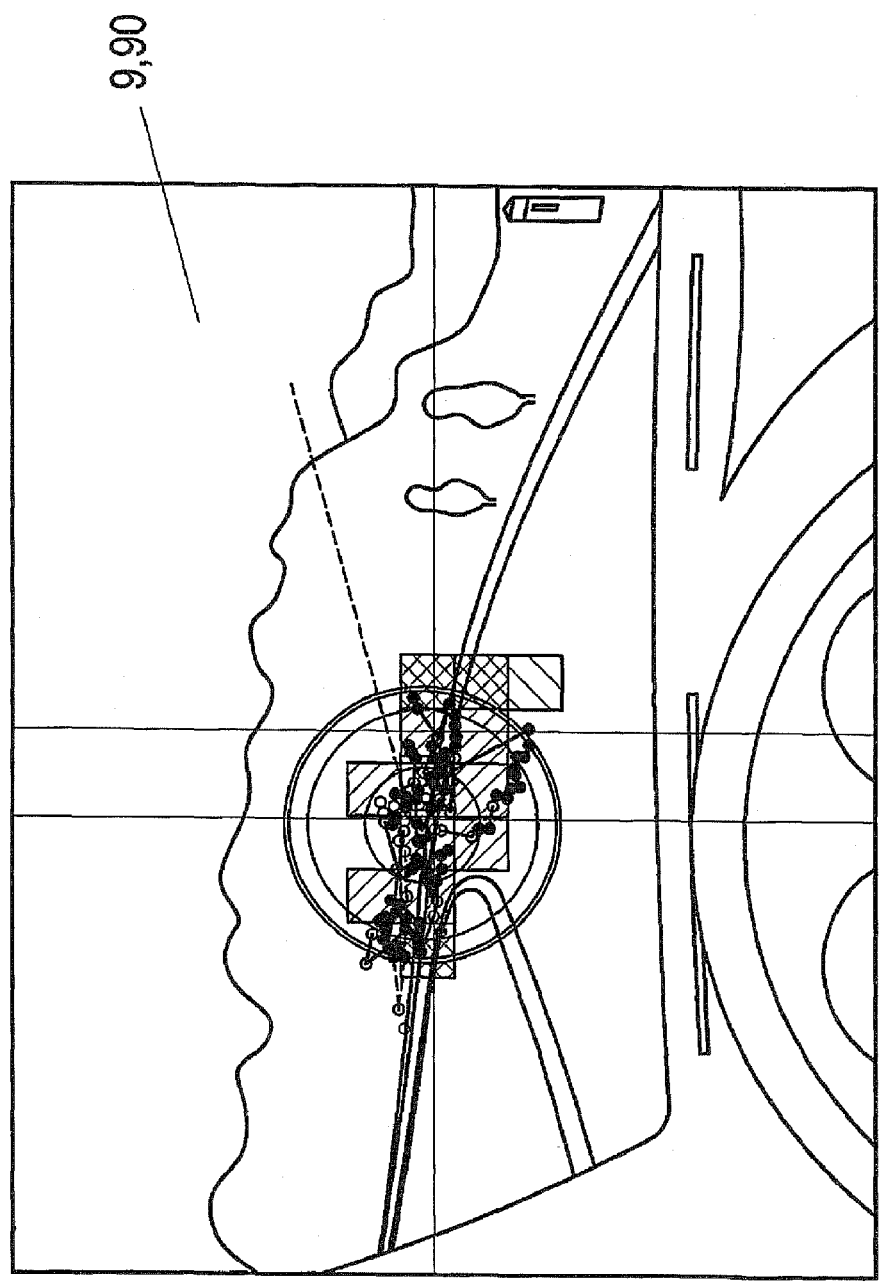
FIG. 27 a twelfth preferred output of a visual field video.

FIG. 26 shows an eleventh preferred output, showing the output methods from FIGS. 17, 19, 20, 24 and 25 overlaid over one another, which means that a particularly large amount of information can be shown in a single illustration, and the observer can evaluate an object or an individual scene particularly quickly and easily. FIG. 27 shows a twelfth preferred output, where the same view as that of FIG. 26 is shown with an image of the first object—in this case an initial scene—behind it, for greater intelligibility.

In addition to the evaluation and/or output procedures described above, it is particularly recommended to provide a further evaluation and/or output procedure as described below, which is especially suited to determining the complexity of a sequence of scenes. As explained on the basis of two examples in FIGS. 28 and 29, this is a particularly useful combination of already described evaluation and/or output processes, which should ideally be augmented by further beneficial evaluations and/or outputs.

Figure 28:
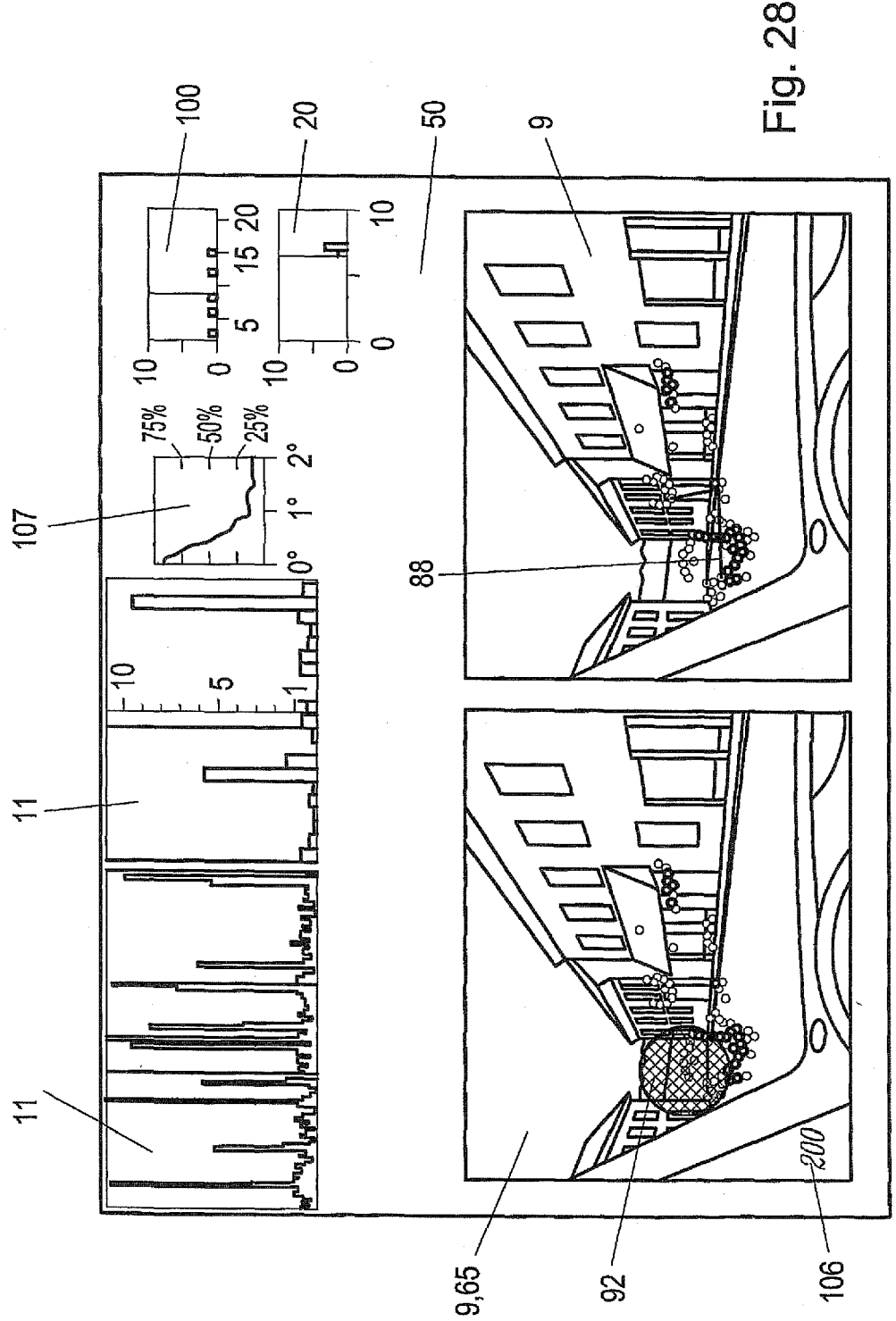
FIG. 28 a preferred output layout in an initial view.
Figure 29:
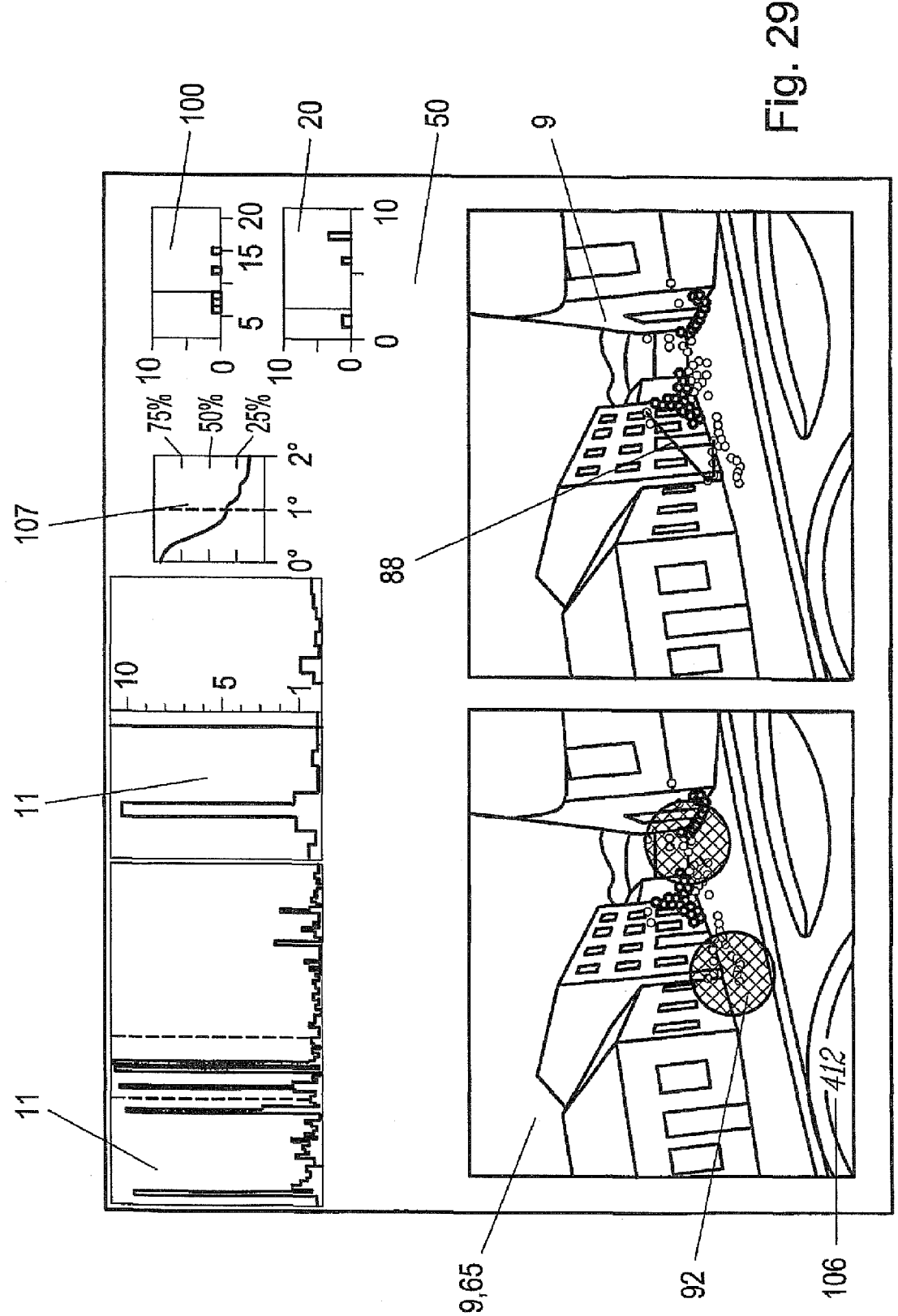
FIG. 29 a preferred output layout in a second view.

FIGS. 28 and 29 show a preferred output template (50), with control tools and other output fields omitted leaving only textual descriptions. The two visual field videos (9), are seen adjacent to one another, with one of the visual field videos (9) showing a representation in accordance with FIG. 17 and the other visual field video (9) showing a representation in accordance with FIG. 25. Also, an initial diagram (11) is provided, as well as a detailed view of this initial diagram (11). The output template (50) also includes an initial saccade diagram (20) and an initial fixation duration diagram (100) for the time being examined, preferably 2 seconds, but to be predetermined. A second diagram (107) is also provided, in which the number of points of vision—and therefore the frequency of the points of vision—and their initial relative distance (40) are arranged around a central visual axis. It is also preferable that for each currently displayed visual field video sequence, the initial fixation duration (103), the saccade angle (52), and a value for the complexity the sequence are given, the value for the complexity being determined from the total measured initial relative angles (42) measured over a predetermined period, generally one second, and displayed This makes it quick and easy to determine whether or not a test subject is overwhelmed by a situation. As soon as the value for the complexity exceeds a predetermined limit value it may be assumed that well-ordered perception of the objects is no longer taking place. Such a situation in road traffic could have disastrous consequences. The use of such a procedure as described above with this kind of evaluation not only enables a situation to be evaluated, but also enables the quick and easy assessment of whether a test subject is fit to drive.

Figure 33:
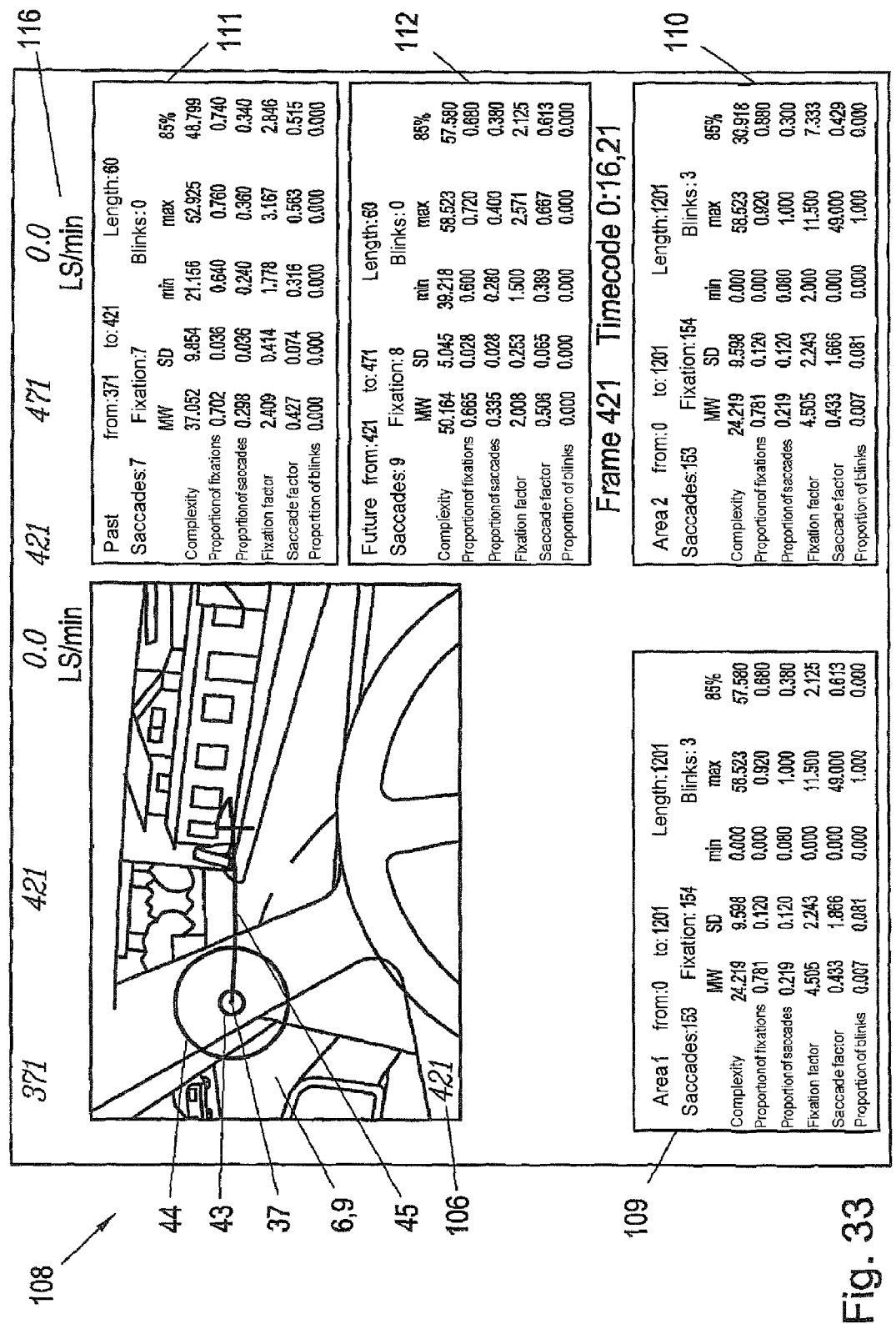
FIG. 33 and FIG. 34 a first example of a preferred output layout for a preferred analysis tool.
Figure 34:
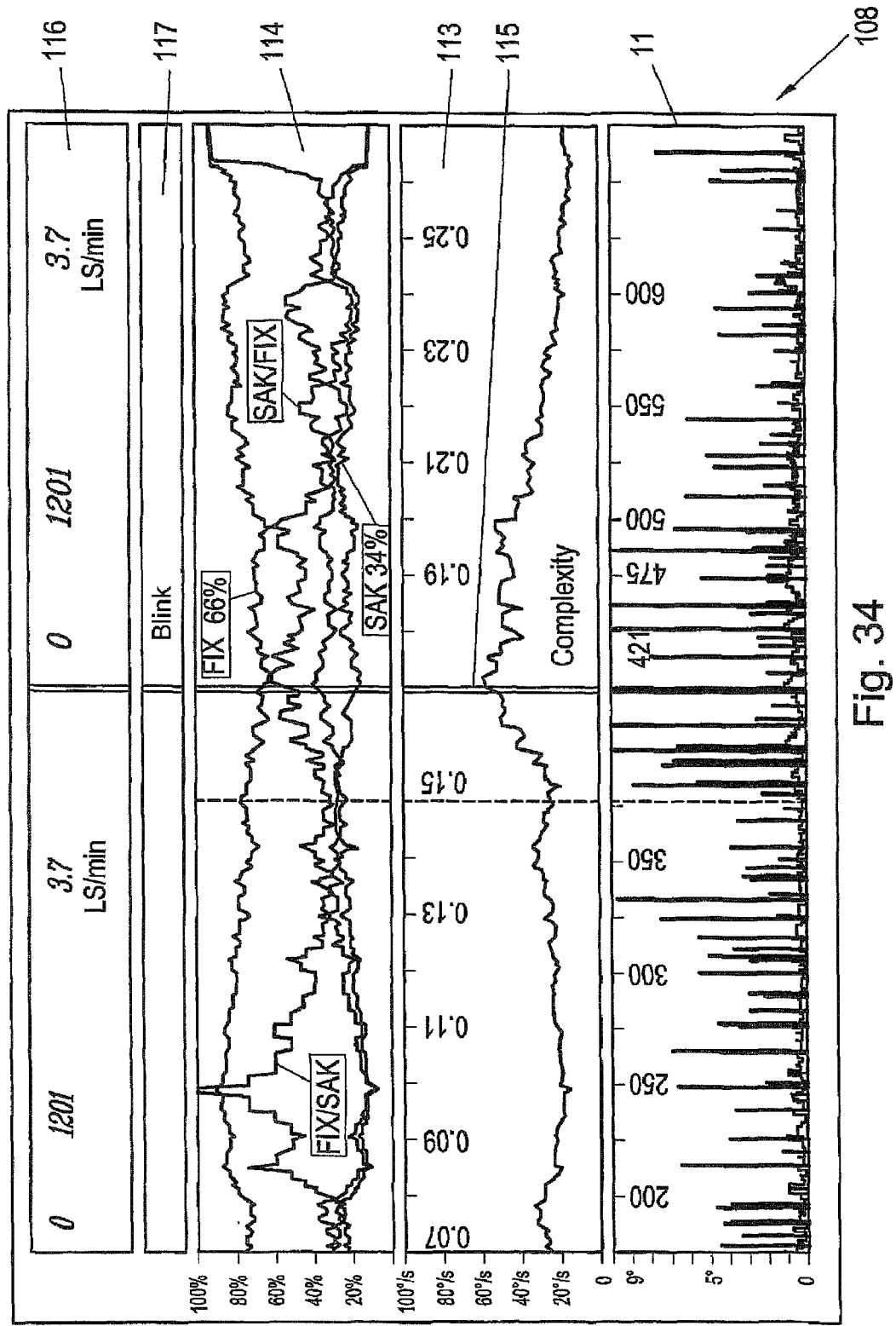
Figure 35:
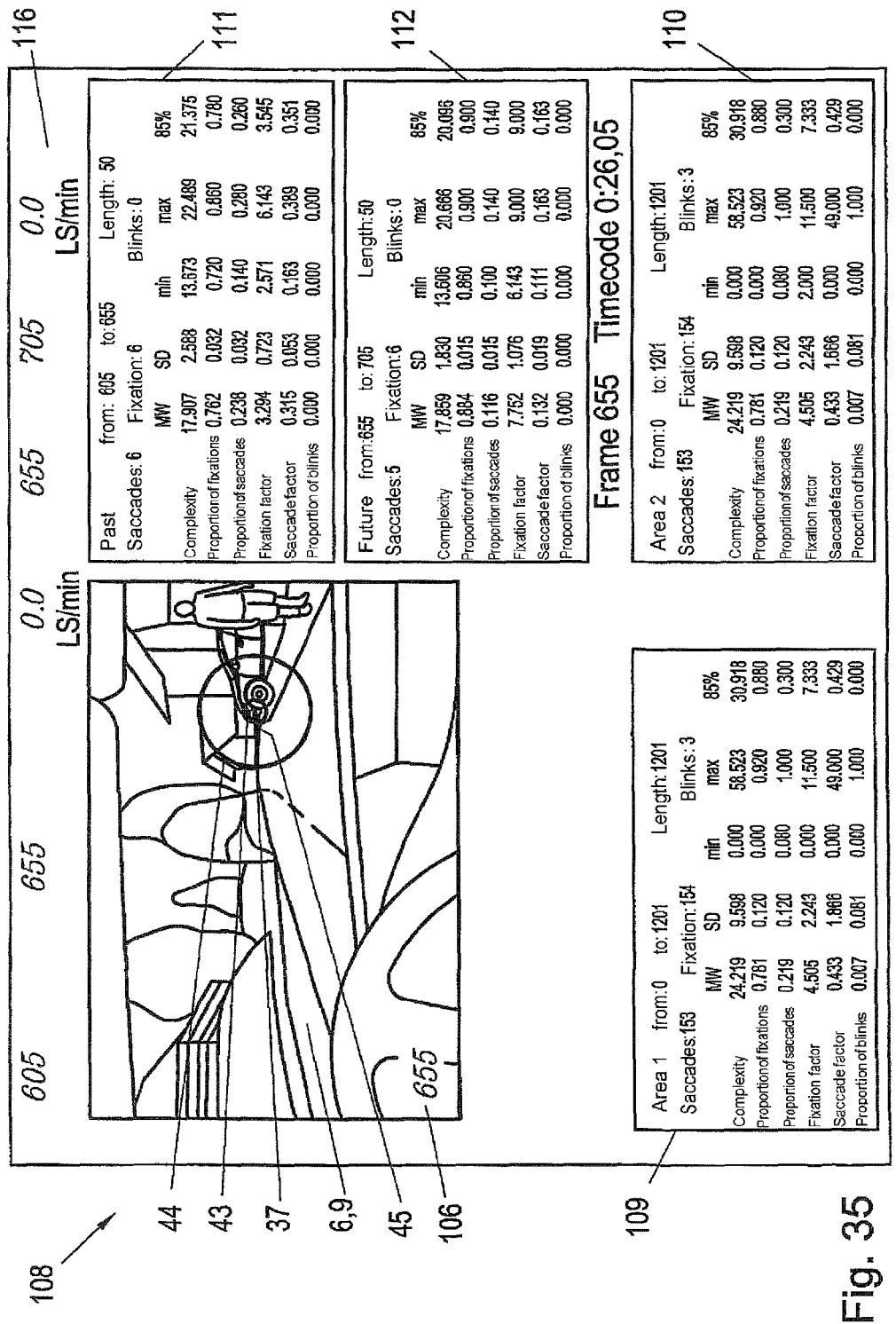
FIG. 35 and FIG. 36 a second example of the preferred output layout for the preferred analysis tool.
Figure 36:
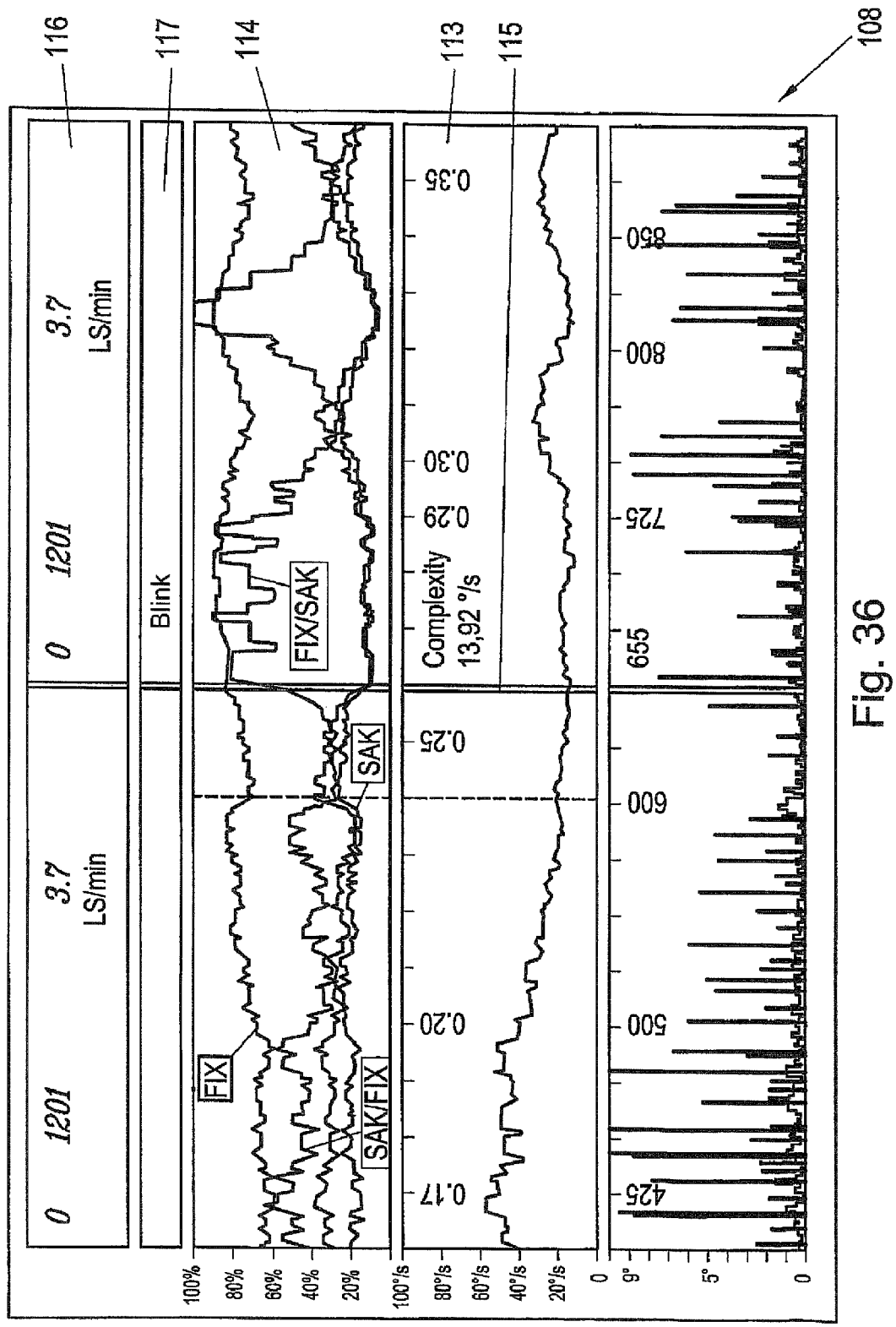

FIGS. 33 to 36 show examples of a preferred output template 108 using a preferred analysis tool, where FIGS. 33 and 34 form a unit and go together and FIGS. 35 and 36 also form a unit and go together. FIGS. 33 and 35 each show a visual field video (9), which, in line with the first preferred output type 6 of a visual field video (9) with a first and second circle (43), (44), is shown in accordance with FIG. 9, whereby the further preferred output types of a visual field video (9) may also be provided. In the visual field video (9) the number of the momentary visual field image or frame is presented as a serial number (106), by means of which an exact assignment of the visual field image shown at a given time within the visual field video (9) is possible. Statistical data for the current visual field video (9) are also determined, preferably calculated by a computer, and shown in an initial report statistics block (109), a second report statistics block (110), as well as a past statistics block (111) and a future statistics block (112). In a first and second report statistics block (109), (110) the statistical data are shown for any given freely-selectable temporary area of the visual field video (9). The past statistics block (111) shows the statistical data for a predetermined time range prior to the moment shown in the visual field image, and the future statistics block (112) shows the statistical data for a predetermined time range after the moment shown in the visual field image.

The individual statistics blocks 109, 110, 111, 112, that is the first and second report statistics blocks (109), (110), the past statistics block (111) and the future statistics block (112), show a complexity value, a fixation proportion, a saccade proportion, a fixation factor, a saccade factor and a blink proportion, where MD represents the arithmetical mean, SD the standard deviation or variance, min the minimum, max the maximum and 85% the 85th percentile of the value in question for the selected time range of the visual field video (9) in each statistics block (109, 110, 111, 112).

The complexity here represents the total of all eye movements in the selected time range of the visual field video (9), preferably given in degrees per time unit, e.g. °/s. The fixation proportion represents the proportion of time in the selected time range of the visual field video (9) that can be assigned to fixations, in relation to the whole duration of the selected time range of the visual field video (9); and the saccade proportion represents the proportion of time in the selected time range of the visual field video (9) that can be assigned to saccades, in relation to the whole duration of the selected time range of the visual field video (9). The fixation proportion and the saccade proportion can each be given values between zero and one and added together give a total of one, as each is only determined using ranges during which there is no blinking causing a temporary complete darkening of the eye.

The fixation factor is the ratio of the proportion of fixations to the proportion of saccades at any given time, and the saccade factor is the ratio of the proportion of saccades to the proportion of fixations at any given time. The blink proportion is the proportion of time taken up by blinks during the selected time range.

The numbers of fixations, saccades and blinks are mainly shown in the relevant statistics blocks (109, 110, 111, 112) and, as illustrated, are also shown as discrete values.

FIG. 34 shows the statistical data for the visual field video (9) and the statistical blocks (109, 110, 111, 112) in accordance with FIG. 33 in graphic form, and FIG. 36 shows this statistical data for the visual field video (9) and the statistical blocks (109, 110, 111, 112) in accordance with FIG. 35 in graphic form. It is preferable to provide, as illustrated, an initial diagram (11) with the graphic representation of the fixations and saccades. The relevant complexity value is also shown in a complexity diagram (113). The further values of the fixations proportion, saccade proportion, fixation factor and/or saccade factor are furthermore shown in an overview diagram (114). The centrally-placed double bar (115) indicates the place shown in the corresponding visual field video (9). Furthermore, blinks are shown both as a numerical blink value (116) and in the form of a blink bar (117).

The analysis tool in accordance with FIGS. 33 to 36 is especially recommended for the determination and detailed examination of points where there is information loss as a result of high complexity or frequent foveal, central visual connections. The output of particularly meaningful statistical values, and their direct assignability to the visual field video (9) shown, enable qualitative in-depth analyses of the real information recording and refined observations of different information deficits and/or information defects to be undertaken. Thus the degree of visual perception can be determined, enabling further medical and neurophysiological investigations to be carried out.

Taking the invention further, provision can be made to evaluate visual perception dimensions together with individual stress parameters (human physiological data) and physical movement and condition values, which means that the procedure described above may also be used in a further context of stress and behavioural research.

The invention also relates to a process for monitoring the visual perception of at least one initial, preferably humanoid user, whereby an initial video of the surroundings of the first user is taken using at least one initial panoramic camera, so that the first video of the surroundings is examined on the basis of the presence of at least one settable pattern, preferably road signs, to determine, using a procedure in accordance with one of Claims 1 to 20, whether the first fixation criterion (25) is complied with in that the initial pattern provides identical points of vision at least in places, and that if this fixation criterion is not fulfilled in the first pattern, at least one control or regulation mechanism is activated. This means that a machine can monitor the visual range of a user together with their viewing behaviour, and, for instance, determine whether certain predetermined ranges or patterns are or have been perceived by the user. For instance, a car may search the street area for road signs, and check whether the driver has actually perceived the road signs. If this is not the case, the car may alert the driver by means of an indicator light or sound, or the car may be automatically stopped if, for example, a stop sign has been missed.

In order to implement a procedure of this kind it is necessary for the pupil movement of the user or the driver to be recorded, for which an appropriate eye tracking system is provided. Although eye tracking systems firmly linked to the head give the best result, an eye tracking system may also be provided that records the pupil movement and line of vision by means of a number of cameras arranged around the user. The preferred application is therefore one in which the user wears goggles or a helmet in any case, as an eye tracking system of this kind can easily be integrated into the helmet or goggles. Possible areas of application include fast-moving machines, such as lathes or rope-making machines, or helmets for fighter aircraft pilots where the aircraft itself searches the surroundings for targets and risks and the pilot is only alerted if he has not perceived these. Systems of this kind could also be integrated into racing drivers' helmets, and may be optimised by means of recognition of the patterns of flag signals at check points etc.

Many aspects of the invention can be seen from the description and the illustrations as well as from the Claims, whereby individual features, including in particular those of the different design forms described, could be implemented on a standalone basis or in the form of a combination with at least one other design form of the invention and/or in other areas, with the provision of any combination of features being possible, which may represent beneficial, patentable inventions in themselves. The division of the present application into several sections does not limit the general validity with regard to the invention of the statements made within these sections.

The invention claimed is:

1. A method for measuring visual perception, comprising the steps of:
    processing at least first visual coordinates of a first point of vision assigned to a first field-of-view image,
    processing at least second visual coordinates of a second point of vision assigned to a second field-of-view image, with the second field-of-view image being recorded after the first field-of-view image,
    examining the second visual coordinates of the second point of vision together with the first visual coordinates of the first point of vision in a comparison device and checking whether they fulfill at least one predetermined first fixation criterion,
    assigning the first and second points of vision, provided they fulfill the at least one first fixation criterion, to a first fixation assigned to an ordered perception, and marking the first and second points of vision as such, and
    assigning the first and second points of vision, if they do not fulfill the at least one first fixation criterion, to a first saccade, to be assigned to aleatoric perception, and marking the first and second points of vision as such.

2. The method of claim 1, further comprising the step of marking an output of the first and second points of vision as belonging to the first fixation or the first saccade.

3. The method of claim 1, wherein the first fixation criterion is a predetermined first distance around the first point of vision, the method further comprising the steps of determining a first relative distance between the first point of vision and the second point of vision, and assigning the first and second points of vision to the first fixation if the first relative distance is less than the first distance.

4. The method of claim 3, wherein the first fixation criterion is predefined.

5. The method of claim 4, wherein the first distance is predefined.

6. The method of claim 4, wherein the predetermined first distance is a first angle of view associated with an area assigned to foveal vision, and wherein the distance between the first point of vision and the second point of vision is a first relative angle.

7. The method of claim 6, wherein the first angle of view is between 0.5° and 1.5°.

8. The method of claim 6, wherein the first angle of view is about 1°.

9. The method of claim 4, wherein the first relative distance is outputted together with the points of vision marked as associated with the first fixation or with the first saccade.

10. The method of claim 4, wherein the first relative distance is outputted in a first diagram over the temporal course of a field-of-view video.

11. The method of claim 1, wherein the second field-of-view image is recorded after a predetermined period of time.

12. The method of claim 11, wherein the predetermined period of time is between 0.005 and 0.1 seconds.

13. The method of claim 12, wherein the predetermined period of time is between 0.02 and 0.04 seconds.

14. The method of claim 1, wherein the second field-of-view image is recorded immediately after the first field-of-view image.

15. The method of claim 1, further comprising the steps of:
    recording a field-of-view video;

determining the visual coordinates of the points of vision, and displaying in a field-of-view video at least the points of vision associated with the first fixation or the first saccade.

16. The method of claim 15, wherein a first circle having a radius equal to the first distance is displayed substantially uniformly around the point of vision together with a point of vision corresponding to the field-of-view image currently shown in the field-of-view video.

17. The method of claim 16, wherein a second circle with a radius equal to a predetermined second distance is displayed substantially uniformly around the point of vision together with a point of vision corresponding to the field-of-view image currently shown in the field-of-view video.

18. The method of claim 17, wherein the second distance is a second angle of view describing an area associated with parafoveal vision.

19. The method of claim 18, wherein the second angle of view is approximately 3° to 5°.

20. The method of claim 15, further comprising the step of connecting sequential points of vision and determining first view traces, which are shown at least temporarily in the field-of-view video.

21. The method of claim 15, wherein the points of vision indicated as being associated with at least the first fixation are displayed as being substantially uniformly enclosed by a third circle, and wherein the radius of the third circle is a function of the continuing duration of the first fixation.

22. The method of claim 15, wherein the field-of-view video is displayed with shading, wherein the points of vision indicated as being associated with at least the first fixation are displayed as being substantially uniformly enclosed by a fourth circle, and wherein the area of the fourth circle is at least temporarily displayed with a lighter shading than the shading of the field-of-view video.

23. The method of claim 15, wherein for a predetermined first section of the field-of-view video, all sequential points of vision satisfying the first fixation criterion are collectively assigned to a first fixation, and wherein an angle distance between the first point of vision associated with the first fixation and the last point of vision associated with the first fixation is determined and outputted as first fixation angle.

24. The method of claim 23, wherein for the first section of the field-of-view video, an angle distance between the last point of vision associated with the first fixation and a first point of vision associated with a second fixation is determined and outputted as first saccade angle.

25. The method of claim 24, wherein for the first section of the field-of-view video, a frequency of the determined fixations is outputted as a function of the first fixation angle.

26. The method of claim 25, wherein for the first section of the field-of-view video, a frequency of the determined saccades is outputted as a function of the saccade angle.

27. The method of claim 23, further comprising the step of accumulating, for a predetermined third section of the field-of-view video, all points of vision associated with a predetermined first object unit in a first object cache for measuring perceptibility of the predetermined first object unit using the points of vision accumulated in the first object cache.

28. The method of claim 1, comprising the steps of:
collectively assigning all sequential points of vision satisfying the first fixation criterion for a predetermined first section of the field-of-view video to a first fixation, and
determining a fixation duration between the first point of vision associated with the first fixation and the last point of vision associated with the first fixation, and
outputting a frequency of the determined fixations are as a function of the first fixation duration.

29. The method of claim 1, wherein for the first section of the field-of-view video, a first saccade duration between the last point of vision associated with the first fixation and a first point of vision associated with a second fixation is determined, and wherein a frequency of the determined saccades is outputted as a function of the first saccade duration.

30. The method of claim 1, further comprising the step of selecting at least one predetermined second fixation criterion different from the first fixation criterion and performing the method steps of claim 27 for at least one predetermined second section of the field-of-view video.

31. The method of claim 30, wherein a frequency of the fixations as a function of at least the first and second fixation criteria is outputted as a first curve with constant first duration and as a second curve with constant second duration.

32. A method for monitoring the visual perception of at least one first, preferably humanoid user, comprising the steps of:
recording a first video of surroundings of a first user using at least one first panoramic camera,
identifying in the first video at least one predetermined pattern, preferably a road sign,
determining with the method of claim 1, whether the first fixation criterion is satisfied by points of vision that overlap with the at least one predetermined pattern at least in areas, and
activating at least one control circuit if the fixation criterion is not satisfied for the at least one predetermined pattern.

33. The method of claim 1, wherein the first visual coordinates and the second visual coordinates are determined using an eye tracking system.

* * * * *

UNITED STATES PATENT AND TRADEMARK OFFICE
CERTIFICATE OF CORRECTION

PATENT NO.        : 8,379,918 B2                               Page 1 of 1
APPLICATION NO.   : 12/664513
DATED             : February 19, 2013
INVENTOR(S)       : Ernst Pfleger et al.

It is certified that error appears in the above-identified patent and that said Letters Patent is hereby corrected as shown below:

Column 24, line 28 (claim 30), change "27" to --1--.

Signed and Sealed this
Ninth Day of April, 2013

Teresa Stanek Rea
*Acting Director of the United States Patent and Trademark Office*